(12) United States Patent
Poritz et al.

(10) Patent No.: US 10,718,013 B2
(45) Date of Patent: Jul. 21, 2020

(54) SAMPLE TO SEQUENCE

(71) Applicants: BioFire Defense, LLC., Salt Lake City, UT (US); BioFire Diagnostics, LLC., Salt Lake City, UT (US)

(72) Inventors: Mark Aaron Poritz, Salt Lake City, UT (US); Kirk Max Ririe, Salt Lake City, UT (US); Christopher Paul Pasko, Salt Lake City, UT (US); Ann Michelle Demogines, Salt Lake City, UT (US); Robert John Crisp, Cottonwood Heights, UT (US); Margarita Rogatcheva, Sandy, UT (US); Robert Cornelius Trauscht, Salt Lake City, UT (US); Matthew Kam Jones, Sandy, UT (US); Tyler Lane Healy, West Jordan, UT (US)

(73) Assignee: BioFire Defense, LLC. et al., Salt Lake City, UT (US)

( * ) Notice: Subject to any disclaimer, the term of this patent is extended or adjusted under 35 U.S.C. 154(b) by 104 days.

(21) Appl. No.: 15/574,263

(22) PCT Filed: Jun. 2, 2016

(86) PCT No.: PCT/US2016/035567
§ 371 (c)(1),
(2) Date: Nov. 15, 2017

(87) PCT Pub. No.: WO2016/196827
PCT Pub. Date: Dec. 8, 2016

(65) Prior Publication Data
US 2018/0135101 A1    May 17, 2018

Related U.S. Application Data

(60) Provisional application No. 62/169,731, filed on Jun. 2, 2015.

(51) Int. Cl.
*C12Q 1/686* (2018.01)
*C12Q 1/6844* (2018.01)
*C12Q 1/6874* (2018.01)

(52) U.S. Cl.
CPC .......... *C12Q 1/686* (2013.01); *C12Q 1/6844* (2013.01); *C12Q 1/6846* (2013.01); *C12Q 1/6874* (2013.01)

(58) Field of Classification Search
None
See application file for complete search history.

(56) References Cited

U.S. PATENT DOCUMENTS

| | | | |
|---|---|---|---|
| 2011/0076674 | A1 | 3/2011 | Blaschke-Bonkowsky |
| 2012/0157322 | A1* | 6/2012 | Myllykangas et al. ..................... C12Q 1/6853 506/2 |
| 2014/0234845 | A1* | 8/2014 | Poritz et al. ........ B01L 3/50273 435/6.12 |

FOREIGN PATENT DOCUMENTS

| | | | |
|---|---|---|---|
| JP | 2008517632 A | 5/2008 | |
| JP | 2008539757 A | 11/2008 | |
| JP | 2009506759 A | 2/2009 | |
| JP | 2009284834 A | 12/2009 | |
| JP | 2010-509918 A | 4/2010 | |
| JP | 2010529862 A | 9/2010 | |
| JP | 2013505442 A | 2/2013 | |
| JP | 2013521780 A | 6/2013 | |
| JP | 2013544498 A | 12/2013 | |
| JP | 2015073479 A | 4/2015 | |
| WO | 2007011867 A1 | 1/2007 | |
| WO | 2007025340 A1 | 3/2007 | |
| WO | WO-2007025340 A1 * | 3/2007 | ........... C12Q 1/6844 |
| WO | 2013158740 A1 | 10/2013 | |
| WO | 2014013263 A1 | 1/2014 | |

* cited by examiner

*Primary Examiner* — Kaijiang Zhang
(74) *Attorney, Agent, or Firm* — Kenneth E. Horton; Kirton McConkie

(57) ABSTRACT

Method and sample vessels are provided for amplification and sequencing of nucleic acids in a sample.

18 Claims, 19 Drawing Sheets

SAMPLE TO SEQUENCE

BACKGROUND

There are a variety of different applications in which a sample-to-sequence result in a short period of time would have great utility. These applications may include rapid, near point-of-care or laboratory, identification of mutations that confer antibiotic resistance, sequencing of viral genes, identification of tissue for forensic purposes, tissue typing for organ transplantation, and identification of alleles related to rates of drug metabolism, for example.

For example, for bacterial pathogens implicated in sepsis, it is useful to know whether the bacteria carry extended spectrum beta-lactamases (ESBLs) that make them resistant to extended spectrum cephalosporins. These ESBLs result from mutations in the TEM-1, TEM-2, SHV, and other beta lactamase genes. There are numerous other genes that can confer an antibiotic resistance phenotype, whose expression or activity is modulated by point mutations in the coding or regulatory regions of these genes. While single known point mutations are easy to assay using standard PCR techniques, mutations in genes that have multiple alleles may be more difficult to identify.

Likewise there are numerous instances in which the sequence of a viral gene can indicate both the presence of that virus in a human sample and whether that virus is resistant to antiviral compounds, and thus indicating what treatment should be started, continued, or stopped. This is true for Hepatitis C, Hepatitis B, and HIV. While time-to-result is not quite as pressing for these chronic viral infections, time is of the essence for other viral infections, such as influenza. With influenza and other acute viral infections, there are an increasing number of well-characterized point mutations that confer resistance to the FDA approved neuraminidase inhibitors. Ideally, treatment with a neuraminidase inhibitor should start as soon as possible after the virus is detected, but it is important that the correct inhibitor be used.

In addition to pathogen detection and identification, there are several instances in which determining the sequence of a human gene or genes quickly is important. These include identification of human tissue for forensic purposes, illustratively by mapping the length of Short Tandem Repeats (STRs). This identification is currently performed by sizing PCR amplicons, but it can also be done by sequencing. A quick sample-to-sequence method would be helpful in many such cases.

Another example is HLA typing an organ for transplantation. Organs to be donated may come from a recently deceased individual. It is important to get the organ delivered quickly to the transplant recipient that has the best MHC match to the donor. The most accurate way to do this is to sequence the MHC genes that govern transplant rejection and then match these sequences to a national registry of recipient MHC types. A quick sample-to-sequence method would be helpful in many organ donation cases.

Yet another example is identification of cytochrome P450 alleles that determine rates of drug metabolism. It is known that cytochrome P450 enzymes in the liver metabolize foreign compounds for excretion. Multiple proteins in this family are known, and different alleles of each are present in different populations and individuals. For example, some people carry alleles for enzymes that metabolize warfarin very fast and some metabolize warfarin much more slowly. Knowing a patient's genotype permits a doctor to decide how much warfarin or other such drugs to administer to achieve a certain level of drug in the blood stream.

Other non-limiting examples where sequencing could be useful includes cancer genes, as well as other infectious agents such as tuberculosis. Many other examples are possible, as are uses both in clinical diagnostics and in other fields.

Polymerase chain reaction (PCR) is a technique widely used in molecular biology. It derives its name from one of its key components, a DNA polymerase used to amplify a piece of DNA by in vitro enzymatic replication. As PCR progresses, the DNA generated (the amplicon) is itself used as a template for replication. This sets in motion a chain reaction in which the DNA template is exponentially amplified. With PCR, it is possible to amplify a single or few copies of a piece of DNA across several orders of magnitude, generating millions or more copies of the DNA piece. PCR employs a thermostable polymerase, dNTPs (deoxynucleotide triphosphates), and a pair of primers (oligonucleotides). Existing PCR techniques and other amplification methods may be combined with next generation sequencing (NGS) to provide quick sample-to-sequence results.

Traditional nucleic acid sequencing techniques employ either chemical cleavage at a specific base (Maxim-Gilbert method) or chain termination using dideoxynucleotides (Sanger sequencing). Next-generation sequencing involves high-throughput sequencing technologies some of which parallelize the sequencing process, producing thousands to millions of sequences concurrently, often detecting as each nucleotide is added to each individual strand. Various next-generation systems are currently available.

BRIEF SUMMARY

In one aspect of the present disclosure, methods for amplification and sequencing of nucleic acids in a sample. Illustrative methods may comprise the steps of placing the sample in an amplification chamber, wherein the amplification chamber is configured for amplifying a plurality of individual nucleic acids that may be present in the sample, subjecting the amplification chamber to amplification conditions, moving the sample to an array of second-stage amplification wells, each second-stage amplification well configured for further amplifying one individual nucleic acid that may be present in the sample, such that a portion of the nucleic acids are moved to each of the additional second-stage amplification wells, performing second-stage amplification in the additional second-stage amplification wells to generate an amplicon in each second-stage amplification well if the individual nucleic acid is present in the sample, and subjecting at least a plurality of the wells to sequencing conditions.

In some embodiments, the systems and methods described herein include methods for amplification and sequencing of nucleic acids in a sample with the methods comprising the steps of placing the sample in a first-stage amplification chamber, where the first-stage amplification chamber is configured for amplifying a plurality of individual nucleic acids that may be present in the sample, subjecting the first-stage amplification chamber to amplification conditions, moving the sample to an array of second-stage amplification wells with each second-stage amplification well configured for further amplifying one individual nucleic acid that may be present in the sample, such that a portion of the sample is moved to each of the second-stage amplification wells, performing second-stage amplification in the second-stage amplification wells to generate an amplicon in each second-stage amplification well if the individual nucleic acid is present in the sample, and subjecting contents of at least one second-stage amplification well to sequencing conditions. In some cases, each of the additional second-stage amplification wells has a primer tethered thereto, and sequencing can occur in the second-stage amplification wells. In other cases, all steps are performed in a single container and the last two steps performed in the wells. In yet other cases, the container is provided with one or more sealable ports, with the sealable ports providing the only access from an exterior of the container to the first-stage amplification chamber and the array of second-stage amplification wells, such that when the one or more sealable ports are sealed, the container is fully closed. In some cases, sequencing can be performed in a separate sample vessel. In other cases, all the steps are performed in about 5 hours or less. In yet other cases, all second-stage amplification wells are subjected to sequencing conditions. In yet other cases, the methods can further comprise the step of detecting whether the amplicon has been generated in each second-stage amplification well to generate a positive call for each second-stage amplification well where the amplicon has been generated. In some instances, sequencing is performed only on those second-stage amplification wells where there is the positive call. In other instances, the first-stage amplification chamber comprises a plurality of first-stage pairs of primers, each of the first-stage pairs of primers configured for amplifying one of the plurality of individual nucleic acids that may be present in the sample, and wherein each of the second-stage amplification wells comprises a pair of second-stage primers configured for amplifying one of the plurality of individual nucleic acids that may be present in the sample. In yet other instances, at least one of each of the pair of second-stage primers is nested within its corresponding first-stage primer.

In some embodiments, the systems and methods described herein include methods for amplification and sequencing of nucleic acids in a sample that comprise the steps of placing the sample in an amplification chamber, where the amplification chamber is configured for amplifying a plurality of individual nucleic acids that may be present in the sample, subjecting the amplification chamber to amplification conditions, moving the sample to an array of spots, each spot comprising a set of second-stage amplification primers tethered thereto, each set of second-stage amplification primers configured for further amplification of one of the individual nucleic acids, performing second-stage amplification on the array to generate an amplicon at each of the spots if that individual nucleic acid is present in the sample, and subjecting at least one of the spots to sequencing conditions. In some instances, all steps are performed in a single container. In other instances, the container is provided with one or more sealable ports, the sealable ports providing the only access from an exterior of the container to the amplification chamber and the array of second-stage amplification wells, such that when the one or more sealable ports are sealed, the container is fully closed. In yet other instances, the array has an inlet channel and an outlet channel and opening and closing the inlet channel and outlet channel controls flow of fluid across the array. In some cases, closure of the outlet channel while fluid enters the inlet channel results in a bubble of fluid over the array, and agitation of the bubble homogenizes the fluid. In other cases, the methods further comprise the step of detecting whether the amplicon has been generated at each spot to generate a positive call for each well where the amplicon has been generated. In yet other cases, the number of spots totals no more than 512 spots. In some instances, the number of spots totals no more than 256 spots. In other instances, the set comprises both of the pair of second-stage primers. In yet other instances, second-stage amplification is performed in the presence of a polymerase having 3' to 5' exonuclease activity. In some cases, the set comprises one of the pair of second-stage primers. In other cases second-stage amplification is performed in the presence of a solution comprising a second of each of the pairs of second-stage primers. In yet other cases, the sample is treated with a polymerase having 3' to 5' exonuclease activity subsequent to subjecting the amplification chamber to amplification. In some instances, all of the second of the pairs of second-stage primers are provided with a 5' sequence corresponding to a universal primer. In other instances, the solution further comprises the universal primer. In yet other instances, all of the second of the pairs of second-stage primers are provided at a concentration no more than about 1/10th the concentration of the universal primer. In some cases, the sample is not diluted between the steps of subjecting the amplification chamber to amplification conditions and performing the second stage amplification. In other cases, at least one of the pair of second-stage primers has an additional sequence corresponding to a universal primer, and sequencing is performed by synthesis using the universal primer.

In some embodiments, the systems and methods described herein include methods for amplification and sequencing of nucleic acids that may be present in a sample, comprising the steps of amplifying in the presence of a plurality of outer primer pairs, each outer primer pair configured for amplifying one of the nucleic acids and in the presence of at least one inner primer for each of the nucleic acids, to generate an amplicon for each of the nucleic acids present in the sample, and subjecting the amplicons to sequencing conditions. In other embodiments, the plurality of outer primer pairs is located in one reaction chamber and the inner primers are located in a separate reaction chamber. In yet other embodiments, the plurality of outer primer pairs and the inner primers are located in a single reaction chamber.

In some embodiments, the systems and methods described herein include methods for amplifying nucleic acids in a sample comprising the steps of placing the sample in a first-stage amplification chamber, where the amplification chamber comprises a first pair of primers configured for amplifying a nucleic acid that may be present in the sample, subjecting the amplification chamber to amplification conditions to generate an amplicon, moving a first portion of the sample to a first second-stage amplification zone comprising a first plurality of sets of second-stage amplification primers, each set of second-stage amplification primers configured to amplify different non-overlapping regions of the amplicon, moving a second portion of the sample to a second second-stage amplification zone comprising a second plurality of sets of second-stage amplification primers, each set of second-stage amplification primers configured to amplify different non-overlapping regions of the amplicon, and performing second-stage amplification on the first second-stage amplification zone to generate first second-stage amplicons and on the second second-stage amplification zone to generate second second-stage amplicons, where at least some of the first second-stage amplicons overlap at least some of the second second-stage amplicons. In other embodiments, the methods further comprise subjecting at least one of the amplicons to sequencing conditions.

In some embodiments, the systems and methods described herein include methods for amplification and sequencing of nucleic acids in a sample comprising the steps of placing the sample in an amplification chamber, wherein the amplification chamber comprises a first forward primer, a second forward primer nested within the first forward primer, and a reverse primer, wherein the second forward primer is tethered to a structure and subjecting the amplification chamber to amplification conditions. In other embodiments, the methods further comprise subjecting the amplification chamber to sequencing conditions.

In some embodiments, the systems and methods described herein include containers for amplification and sequencing of a plurality of nucleic acids comprising a first-stage amplification chamber, the first-stage amplification chamber comprising a plurality of first-stage pairs of primers, each first-stage pair of primers configured for amplification of one of the plurality of nucleic acids to generate first-stage amplicons and a second-stage amplification chamber, the second-stage amplification chamber comprising a plurality of second-stage primer pairs, each second-stage pair of primers configured for amplification of at least a portion of a sequence of one of the first stage-amplicons to generate second-stage amplicons, where the second-stage amplification chamber is further configured for sequencing the second-stage amplicons. In some cases, at least one member of each of the second-stage primer pairs is nested within a corresponding first-stage primer. In other cases, at least one member of each of the second-stage primer pairs is tethered to a support. In yet other cases, the at least one member of each of the second-stage primer pairs is tethered to the support by the 5' end. In some instances, the second-stage amplicons comprise single molecular species. In other instances, the containers further comprise one or more sealable ports, the one or more sealable ports providing the only access from an exterior of the container to the first amplification chamber and the second-stage amplification chamber, such that when the one or more sealable ports are sealed, the container is fully closed. In yet other instances, the second-stage amplification chamber comprises an inlet channel and an outlet channel and opening and closing the inlet channel and the outlet channel controls flow of fluid across the second-stage amplification chamber. In some cases, the containers further comprise a lysis chamber configured to receive a sample and to prepare a lysed sample. In other cases, the containers further comprise a nucleic acid extraction chamber configured to receive the lysed sample and to extract nucleic acids from the lysed sample. In some instances, the second-stage amplification chamber comprises an array of wells, each well configured to carry out a second-stage amplification reaction. In other instances, the second-stage amplification chamber comprises an array of spots, each spot comprising second-stage primer pairs, and each spot configured to carry out a second-stage amplification reaction. In yet other instances, at least one of the second-stage primers is tethered to the spot. In some cases, the number of spots totals no more than 512 spots. In other cases, the number of spots totals no more than 256 spots.

In some embodiments, the systems and methods described herein include methods for two-step amplification and sequencing of a plurality of nucleic acids that may be in a sample comprising amplifying the nucleic acids in a first mixture comprising a plurality of first-stage pairs of primers, each first-stage pair of primers configured for amplification of one of the plurality of nucleic acids to generate a first-stage amplicon for each of the nucleic acids that are present in the sample, amplifying the first-stage amplicons using a plurality of second-stage pairs of primers, each second-stage pair of primers configured for amplification of one of the first-stage amplicons, wherein at least one of each pair of second-stage primers is nested within its corresponding first-stage pair of primers, to generate a single molecular species for each of the nucleic acids that are present in the sample, and sequencing the single molecular species that are generated. In other embodiments, the steps of amplifying and sequencing are performed in a single reaction chamber. In yet other embodiments, at least one of each pair of second-stage primers is tethered to a solid support. In some embodiments, the steps of amplifying and sequencing are performed in different reaction vessels. In other embodiments, no filter is used between the steps of amplifying and sequencing to identify the correct amplicon.

Additional features and advantages of the embodiments of the invention will be set forth in the description which follows or may be learned by the practice of such embodiments. The features and advantages of such embodiments may be realized and obtained by means of the instruments and combinations particularly pointed out in the appended claims. These and other features will become more fully apparent from the following description and appended claims, or may be learned by the practice of such embodiments as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 7A shows overlapping second-stage amplicons, while FIGS. 7A-7B shows one way of dividing second-stage amplification into second-stage amplification reactions.

DETAILED DESCRIPTION

Figure 1:
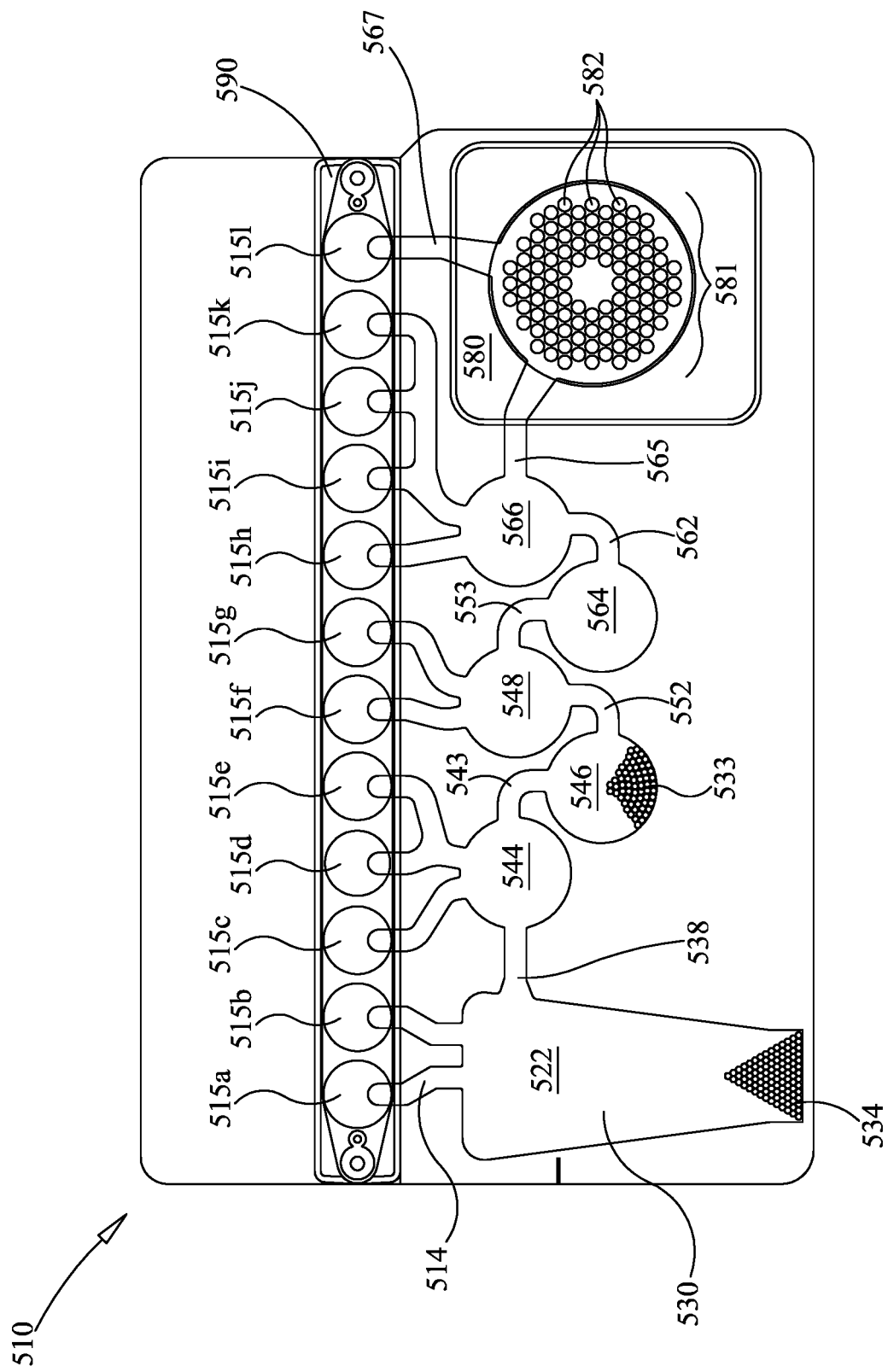
FIG. 1 shows an illustrative pouch for use in one embodiment in this disclosure.

Before describing example implementations in detail, it is to be understood that this disclosure is not limited to parameters of the particularly exemplified systems, methods, apparatus, products, processes, compositions, and/or kits, which may, of course, vary. It is also to be understood that the terminology used herein is only for the purpose of describing particular implementations of the present disclosure, and is not necessarily intended to limit the scope of the disclosure and/or invention in any manner. Thus, while the present disclosure will be described in detail with reference to specific configurations, the descriptions are illustrative only and are not to be construed as limiting the scope of the claimed invention. For instance, certain implementations may include fewer or additional components than those illustrated in the accompanying drawings and/or described in the written description. Furthermore, various modifications can be made to the illustrated configurations without departing from the spirit and scope of the invention as defined by the claims. Thus, while various aspects, embodiments, and/or implementations of the invention are described and/or disclosed herein, other aspects, implementations, and embodiments are also contemplated.

Unless defined otherwise, all technical and scientific terms used herein have the same meaning as commonly understood by one of ordinary skill in the art to which the present disclosure pertains. While a number of methods and materials similar or equivalent to those described herein can be used in the practice of the present disclosure, only certain exemplary materials and methods are described herein.

Various aspects of the present disclosure, including devices, systems, methods, etc., may be illustrated with reference to one or more exemplary implementations. As used herein, the terms "exemplary" and "illustrative" mean "serving as an example, instance, or illustration," and should not necessarily be construed as preferred or advantageous over other implementations disclosed herein. In addition, reference to an "implementation" or "embodiment" of the present disclosure or invention includes a specific reference to one or more embodiments thereof, and vice versa, and is intended to provide illustrative examples without limiting the scope of the invention, which is indicated by the appended claims rather than by the following description.

It will be noted that, as used in this specification and the appended claims, the singular forms "a," "an" and "the" include plural referents unless the content clearly dictates otherwise. Thus, for example, reference to "a tile" includes one, two, or more tiles. Similarly, reference to a plurality of referents should be interpreted as comprising a single referent and/or a plurality of referents unless the content and/or context clearly dictate otherwise. Thus, reference to "tiles" does not necessarily require a plurality of such tiles. Instead, it will be appreciated that independent of conjugation; one or more tiles are contemplated herein.

As used throughout this application the words "can" and "may" are used in a permissive sense (i.e., meaning having the potential to), rather than the mandatory sense (i.e., meaning must). Additionally, the terms "including," "having," "involving," "containing," "characterized by," variants thereof (e.g., "includes," "has," and "involves," "contains," etc.), and similar terms as used herein, including the claims, shall be inclusive and/or open-ended, shall have the same meaning as the word "comprising" and variants thereof (e.g., "comprise" and "comprises"), and do not exclude additional, un-recited elements or method steps, illustratively.

As used herein, directional and/or arbitrary terms, such as "top," "bottom," "left," "right," "up," "down," "upper," "lower," "inner," "outer," "internal," "external," "interior," "exterior," "proximal," "distal," "forward", "reverse", and the like can be used solely to indicate relative directions and/or orientations and may not be otherwise intended to limit the scope of the disclosure, including the specification, invention, and/or claims.

It is also understood that various implementations described herein can be utilized in combination with any other implementation described or disclosed, without departing from the scope of the present disclosure. Therefore, products, members, elements, devices, apparatus, systems, methods, processes, compositions, and/or kits according to certain implementations of the present disclosure can include, incorporate, or otherwise comprise properties, features, components, members, elements, steps, and/or the like described in other implementations (including systems, methods, apparatus, and/or the like) disclosed herein without departing from the scope of the present disclosure. Thus, reference to a specific feature in relation to one implementation should not be construed as being limited to applications only within said implementation.

The headings used herein are for organizational purposes only and are not meant to be used to limit the scope of the description or the claims. To facilitate understanding, like reference numerals have been used, where possible, to designate like elements common to the figures. Furthermore, where possible, like numbering of elements have been used in various figures. Furthermore, alternative configurations of a particular element may each include separate letters appended to the element number.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 5%. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

The word "or" as used herein means any one member of a particular list and also includes any combination of members of that list.

By "sample" is meant an animal; a tissue or organ from an animal; a cell (either within a subject, taken directly from a subject, or a cell maintained in culture or from a cultured cell line); a cell lysate (or lysate fraction) or cell extract; a solution containing one or more molecules derived from a cell, cellular material, or viral material (e.g. a polypeptide or nucleic acid); a virus; a solution containing one or more molecules derived from a virus; a parasite; a solution containing one or more molecules derived from a parasite; a bacterium, a solution containing one or more molecules derived from a bacterium, a fungus; a solution containing one or more molecules derived from a fungus; a plant; a solution containing one more molecules derived from a plant; or a solution containing a nucleic acid, which is assayed as described herein. A sample may also be any body fluid or excretion (for example, but not limited to, blood, urine, stool, saliva, tears, bile, cerebrospinal fluid, mucous, pus, sweat) that contains cells, cell components, or nucleic acids.

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages), or the expanded genetic alphabet described by, for example, Benner U P U.S. Pat. No. 8,354,225, "Amplification of oligonucleotides containing non-standard nucleobases" and U.S. Pat. No. 8,871,469 "Self-avoiding molecular recognition systems in DNA priming". In particular, nucleic acids can include, without limitation, DNA, RNA, cDNA, gDNA, ssDNA, dsDNA or any combination thereof.

By "probe," "primer," or "oligonucleotide" is meant a single-stranded nucleic acid molecule of defined sequence that can base-pair to a second nucleic acid molecule that contains a complementary sequence (the "target"). The stability of the resulting hybrid depends upon the length, GC content, and the extent of the base-pairing that occurs. The extent of base-pairing is affected by parameters such as the degree of complementarity between the probe and target molecules and the degree of stringency of the hybridization conditions. The degree of hybridization stringency is affected by parameters such as temperature, salt concentration, and the concentration of organic molecules such as formamide, and is determined by methods known to one skilled in the art. Probes, primers, and oligonucleotides may be detectably-labeled, either radioactively, fluorescently, or non-radioactively, by methods well-known to those skilled in the art. dsDNA binding dyes may be used to detect dsDNA. It is understood that a "primer" is specifically configured to be extended by a polymerase, whereas a "probe" or "oligonucleotide" may or may not be so configured.

By "dsDNA binding dyes" is meant dyes that fluoresce differentially when bound to double-stranded DNA than when bound to single-stranded DNA or free in solution, usually by fluorescing more strongly. While reference is made to dsDNA binding dyes, it is understood that any suitable dye may be used herein, with some non-limiting illustrative dyes described in U.S. Pat. No. 7,387,887, herein incorporated by reference. Other signal producing substances also may be used for detecting nucleic acid amplification and melting, illustratively enzymes, antibodies, etc., as are known in the art.

By "specifically hybridizes" is meant that a probe, primer, or oligonucleotide recognizes and physically interacts (that is, base-pairs) with a substantially complementary nucleic acid (for example, a sample nucleic acid) under high stringency conditions, and does not substantially base pair with other nucleic acids.

By "high stringency conditions" is meant conditions configured to allow for identification of target nucleic acid sequences. Such conditions typically occur at about Tm minus 5° C. (5° below the Tm of the probe). Functionally, high stringency conditions are used to identify nucleic acid sequences having at least 80% sequence identity.

While PCR is the amplification method used in the examples herein, it is understood that any amplification method that uses a primer may be suitable. Such suitable procedures include polymerase chain reaction (PCR); strand displacement amplification (SDA); nucleic acid sequence-based amplification (NASBA); cascade rolling circle amplification (CRCA), loop-mediated isothermal amplification of DNA (LAMP); isothermal and chimeric primer-initiated amplification of nucleic acids (ICAN); target based-helicase dependent amplification (HDA); transcription-mediated amplification (TMA), and the like. Therefore, when the term PCR is used, it should be understood to include other alternative amplification methods. For amplification methods without discrete cycles, reaction time may be used where measurements are made in cycles or Cp, and additional reaction time may be added where additional PCR cycles are added in the embodiments described herein. It is understood that protocols may need to be adjusted accordingly.

In some embodiments, PCR includes any suitable PCR method. For example, PCR can include multiplex PCR in which the polymerase chain reaction is used to amplify several different nucleic acid sequences simultaneously. Multiplex PCR can use multiple primer sets and can amplify several different nucleic acid sequences at the same time. In some cases, multiplex PCR can employ multiple primer sets within a single PCR reaction to produce amplicons of different nucleic acid sequence that are specific to different nucleic acid target sequences. Multiplex PCR can have the helpful feature of generating amplicons of different nucleic acid target sequences with a single PCR reaction instead of multiple individual PCR reactions.

As used herein, "sequencing" means identifying the sequence of a nucleic acid, including identifying the sequence of one or both strands of the nucleic acid, to determine a sequential order of the individual bases. "Next-generation sequencing" is sequencing performed on a plurality of simultaneous parallel reactions.

The following nomenclature for oligonucleotides is used herein:

U=Universal primer—common sequence shared by all primers in a particular reaction S=Specific primer—unique to a given target assay Subscripts:

o=outer—primer used in the first-stage amplification to generate the outer amplicon i=inner—a nested primer used in the second-stage amplification reaction. This primer can partially overlap the outer primer that was used to generate the outer amplicon, but lies partially or wholly inside the outer amplicon ii=inner-inner—a primer that nests inside of the nested inner primer. This primer can partially overlap this inner primer or sit wholly inside the inner primer F=Forward and R=Reverse—are the two primers that define a PCR amplicon. It is understood that the orientation is arbitrary x=index of a particular specific oligonucleotide in the multiplex (1≤x≤n)

For example: $U_R S_{iR4}$ is a universal reverse primer on the 5' end of Specific inner reverse for amplicon number 4.

While various examples herein reference human targets and human pathogens, these examples are illustrative only. Methods, kits, and devices described herein may be used to detect and sequence a wide variety of nucleic acid sequences from a wide variety of samples, including, but not limited to human samples, animal sample, veterinary samples, plant samples, algae samples, food samples, industrial samples, viral samples, fungus samples, bacteria samples, parasite samples, and environmental samples. The methods, kits, and devices described herein may be used to detect and sequence a wide variety of nucleic acid sequences from a wide variety of applications including, but not limited to, detecting antibiotic resistance, detecting viral genes, forensics, tissue typing, organ transplantation, drug metabolism, bioterrorism, food safety, environmental safety, agriculture, and ecology.

Various embodiments disclosed herein use a self-contained nucleic acid analysis pouch to assay a sample for the presence of and/or identification of various biological substances, illustratively antigens and nucleic acid sequences, illustratively in a single closed system. Such systems, including pouches and instruments for use with the pouches, are disclosed in more detail in U.S. Pat. Nos. 8,394,608; and 8,895,295; and U.S. Patent Application No. 2014-0283945, herein incorporated by reference. However, it is understood that such pouches are illustrative only, and the PCR reactions discussed herein may be performed in any of a variety of open or closed system sample vessels as are known in the art, including 96-well plates, plates of other configurations, arrays, carousels, and the like, using a variety of amplification systems, as are known in the art. While the terms "sample well", "amplification well", "amplification container", or the like are used herein, these terms are meant to encompass wells, tubes, DNA chips, and various other reaction containers, as are used in these amplification systems. In one embodiment, the pouch is used to assay for multiple target nucleic acids. The pouch may include one or more blisters used as sample wells, illustratively in a closed system. Illustratively, various steps may be performed in the optionally disposable pouch, including nucleic acid preparation, primary large volume multiplex PCR, dilution of primary amplification product, and secondary PCR, culminating with optional real-time detection or post-amplification analysis such as melting-curve analysis and nucleic acid sequencing. Further, it is understood that while the various steps may be performed in pouches of the present invention, one or more of the steps may be omitted for certain uses, and the pouch configuration may be altered accordingly.

FIG. 1 shows an illustrative pouch 510 that may be used in various embodiments, or may be reconfigured for various embodiments. Pouch 510 is similar to FIG. 15 of U.S. Pat. No. 8,895,295, with like items numbered the same. Fitment 590 is provided with entry channels 515a through 515l, which also serve as reagent reservoirs or waste reservoirs. Illustratively, reagents may be freeze dried in fitment 590 and rehydrated prior to use. Blisters 522, 544, 546, 548, 564, and 566, with their respective channels 538, 543, 552, 553, 562, and 565 are similar to blisters of the same number of FIG. 15 of U.S. Pat. No. 8,895,295. Second-stage reaction zone 580 of FIG. 1 is similar to that of U.S. Pat. No. 8,895,295, but the second-stage wells 582 of high density array 581 are arranged in a somewhat different pattern. The more circular pattern of high density array 581 of FIG. 1 eliminates wells in corners and may result in more uniform filling of second-stage wells 582. As shown, the high density array 581 is provided with 102 second-stage wells 582. Pouch 510 is suitable for use in the FilmArray instrument (BioFire Diagnostics, Salt Lake City, Utah). However, it is understood that the pouch embodiment is illustrative only.

Pouch 510 may be used in a manner similar to that described in U.S. Pat. No. 8,895,295. In one illustrative embodiment, a 300 μl mixture comprising the sample to be tested (100 μl) and lysis buffer (200 μl) is injected into injection port (not shown) in fitment 590 near entry channel 515a, and the sample mixture is drawn into entry channel 515a. Water is also injected into a second injection port (not shown) of the fitment 590 adjacent entry channel 515l, and is distributed via a channel (not shown) provided in fitment 590, thereby hydrating up to eleven different reagents, each of which were previously provided in dry form at entry channels 515b through 515l via. These reagents illustratively may include freeze-dried PCR reagents, DNA extraction reagents, wash solutions, immunoassay reagents, or other chemical entities. Illustratively, the reagents are for nucleic acid extraction, first-stage multiplex PCR, dilution of the multiplex reaction, and preparation of second-stage PCR reagents, as well as control reactions. In the embodiment shown in FIG. 1, all that need be injected is the sample solution in one injection port and water in the other injection port. After injection, the two injection ports may be sealed. For more information on various configurations of pouch 510 and fitment 590, see U.S. Pat. No. 8,895,295, already incorporated by reference.

After injection, the sample is moved from injection channel 515a to lysis blister 522 via channel 514. Lysis blister 522 is provided with ceramic beads 534 and is configured for vortexing via impaction using rotating blades or paddles provided within the FilmArray instrument. Once the cells have been adequately lysed, the sample is moved through channel 538, blister 544, and channel 543, to blister 546, where the sample is mixed with nucleic acid-binding magnetic beads, such as silica-coated magnetic beads 533. The mixture is allowed to incubate for an appropriate length of time, illustratively approximately 10 seconds to 10 minutes. A retractable magnet located within the FilmArray instrument adjacent blister 546 captures the magnetic beads from the solution, forming a pellet against the interior surface of blister 546. The liquid is then moved out of blister 546 and back through blister 544 and into blister 522, which is now used as a waste receptacle. One or more wash buffers from one or more of injection channels 515c to 515e are provided via blister 544 and channel 543 to blister 546. Optionally, the magnet is retracted and the magnetic beads are washed by moving the beads back and forth from blisters 544 and 546 via channel 543. Once the magnetic beads are washed, the magnetic beads are recaptured in blister 546 by activation of the magnet, and the wash solution is then moved to blister 522. This process may be repeated as necessary to wash the lysis buffer and sample debris from the nucleic acid-binding magnetic beads.

After washing, elution buffer stored at injection channel 515f is moved to blister 548, and the magnet is retracted. The solution is cycled between blisters 546 and 548 via channel 552, breaking up the pellet of magnetic beads in blister 546 and allowing the captured nucleic acids to dissociate from the beads and be released into solution. The magnet is once again activated, capturing the magnetic beads in blister 546, and the eluted nucleic acid solution is moved into blister 548.

First-stage PCR master mix from injection channel 515g is mixed with the nucleic acid sample in blister 548. Optionally, the mixture is mixed by forcing the mixture between 548 and 564 via channel 553. After several cycles of mixing, the solution is contained in blister 564, where a pellet of first-stage PCR primers is provided, at least one set of primers for each target nucleic acid sequence, and first-stage multiplex PCR is performed. If RNA targets are present, an RT (reverse transcription) step may be performed prior to or simultaneously with the first-stage multiplex PCR. First-stage multiplex PCR temperature cycling in the FilmArray instrument is illustratively performed for 15-30 cycles, although other levels of amplification may be desirable, depending on the requirements of the specific application. The first-stage PCR master mix may be any of various master mixes, as are known in the art. In one illustrative example, the first-stage PCR master mix may be any of the chemistries disclosed in U.S. Ser. No. 14/403,369 and WO2013/177429, already incorporated by reference, for use with PCR protocols taking 20 seconds or less per cycle.

After first-stage PCR has proceeded for the desired number of cycles, the sample may be diluted, illustratively by forcing most of the sample back into blister 548, leaving only a small amount in blister 564, and adding second-stage PCR master mix from injection channel 515*i*. Alternatively, a dilution buffer from 515*i* may be moved to blister 566 then mixed with the amplified sample in blister 564 by moving the fluids back and forth between blisters 564 and 566. If desired, dilution may be repeated several times, using dilution buffer from injection channels 515*j* and 515*k*, or injection channel 515*k* may be reserved for sequencing, as discussed below, and then adding second-stage PCR master mix from injection channel 515*h* to some or all of the diluted amplified sample. It is understood that the level of dilution may be adjusted by altering the number of dilution steps or by altering the percentage of the sample discarded prior to mixing with the dilution buffer or second-stage PCR master mix comprising components for amplification, illustratively a polymerase, dNTPs, and a suitable buffer, although other components may be suitable, particularly for non-PCR amplification methods. If desired, this mixture of the sample and second-stage PCR master mix may be pre-heated in blister 564 prior to movement to second-stage wells 582 for second-stage amplification. Such preheating may obviate the need for a hot-start component (antibody, chemical, or otherwise) in the second-stage PCR mixture.

The illustrative second-stage PCR master mix is incomplete, lacking primer pairs, and each of the 102 second-stage wells 582 is individually pre-loaded with a specific PCR primer pair. If desired, second-stage PCR master mix may lack other reaction components, and these components may be pre-loaded in the second-stage wells 582 as well. Each primer pair may be similar to or identical to a first-stage PCR primer pair or may be nested within the first-stage primer pair. It is understood that nested primers are primers that hybridize to the first-stage amplicon in a position that is internal to the hybridization location of the first-stage primers. A nested primer may partially overlap the first-stage primer but the 3'-end is located internally to the 3'-end of the first-stage primer. Movement of the sample from blister 564 to the second-stage wells 582 completes the PCR reaction mixture. Once high density array 581 is filled, the individual second-stage reactions are sealed in their respective second-stage blisters by any number of means, as is known in the art. Illustrative ways of filling and sealing the high density array 581 without cross-contamination are discussed in U.S. Pat. No. 8,895,295, already incorporated by reference. Illustratively, the various reactions in wells 582 of high density array 581 are simultaneously thermal cycled to carry out the second-stage PCR reaction, illustratively with one or more peltier devices, although other means for thermal cycling are known in the art.

In certain embodiments, second-stage PCR master mix contains the dsDNA binding dye LCGreen® Plus to generate a signal indicative of amplification. However, it is understood that this dye is illustrative only, and that other signals may be used, including other dsDNA binding dyes, and probes that are labeled fluorescently, radioactively, chemiluminescently, enzymatically, or the like, as are known in the art. Alternatively, wells 582 of array 581 may be provided without a signal, with results reported through subsequent sequencing.

The illustrative FilmArray instrument can be programmed to make positive or negative calls for each second-stage reaction based on a post-PCR melt. A positive call can indicate a successful second-stage PCR reaction for a corresponding well 582. A positive call can also indicate that the quality of the amplicon generated in the second-stage PCR reaction is sufficient to permit sequencing. A positive call can also indicate that the second-stage PCR reaction has produced an amplicon that is a substantially homogeneous molecular species. A negative call can indicate an unsuccessful second-stage PCR reaction for a corresponding well 582. A negative call can also indicate that the quality of the amplicon generated in the second-stage PCR reaction is not of sufficient to permit sequencing. A negative call can also indicate that the second-stage PCR reaction has not produced an amplicon that is a substantially homogeneous molecular species. In one embodiment, the melt curve must produce a melt peak (e.g., first derivative maximum or negative first derivative maximum) within a pre-defined temperature range, for the call to be positive. It is understood that this method of calling each second-stage reaction is illustrative only, and that calls could be made using real-time amplification data or by other means, as are known in the art, or calls may be deferred until subsequent sequencing is performed.

Illustratively, if the instrument is configured to make positive or negative calls, the instrument may be programmed to earmark only those wells that produce a positive result for subsequent sequencing. In some embodiments, there may be a one-to-one unity between positive calls and the wells earmarked for sequencing. In other embodiments, the wells earmarked for sequencing may not have one-to-one unity with the wells that produce a positive call. For example, the second-stage 580 of the FilmArray pouch 510 may be spotted with replicate wells, illustratively duplicate or triplicate wells. If one or more of those wells come up positive, it may be desirable for all replicates of that target sequence to be earmarked for sequencing. In other embodiments, it may be desirable to earmark only one well for each replicate for sequencing. In yet other embodiments, wells that are used as controls may or may not be earmarked for subsequent sequencing. In yet other embodiments, all wells may be sequenced, with or without positive or negative amplification calls.

While the FilmArray is useful in providing positive or negative results based on PCR from a crude biological sample, methods of going from a crude biological sample to the sequence of specific RNA and DNA targets also would be useful. In one illustrative embodiment, the procedure may be automated, may take less than 8 hours, more illustratively less than 5 hours, and more illustratively take 3 hours or less, and may provide 25 or more bases of sequence, illustratively up to 200 bases of sequence for multiple amplicons, and illustratively up 1000 amplicons. Illustratively, crude sample-to-sequence processes will occur in a closed system so as to minimize the chance of amplicon contamination.

The second-stage 580 of the FilmArray pouch 510 is used to generate amplicons for the desired target. Because of the two-step PCR, essentially homogeneous amplicons are generated in each of the second-stage wells 582. Each batch of amplicons in its respective well 582 may be independently sequenced by sequencing methods known in the art. For example, each batch of amplicons can be sequenced by any one of several techniques known in the art for Next Generation Sequencing (NGS), such as Ion Torrent (Life Technologies), 454 (Roche), SOLiD (ABI), HiSeq or MiSeq (Illumina), and Pacific Biosciences.

In many successful FilmArray pouch runs, a positive signal in a well 582 in the second-stage array 581 represents a substantially pure single species of amplicon. This single species of amplicon is not necessarily a molecular clone. For example, digital PCR, emulsion PCR, or molecular cloning into a plasmid are all methods that generate spatially separated molecular clones of an original nucleic acid molecule. In contrast, the second-stage amplicon originates from many identical or closely related template molecules. However, because of the first-stage enrichment and dilution, the end result of the second-stage PCR is predominantly a single species of amplicon, referred to herein as a "single molecular species". It is understood that, as used herein, a single molecular species will not necessarily be a molecular clone, but will be sufficiently one predominant species to enable sequencing.

In some embodiments, melting curves of the amplicons generated in the second-stage PCR indicate that these amplicons are essentially homogeneous. That the melting curve analysis is performed on the FilmArray instrument with the non-specific double-stranded DNA binding dye LCGreen® Plus and results in single peaks and indicates that the second-stage PCR product is dominated by a single intended amplicon and does not include a significant amount of primer-dimer species or non-specific amplicons, demonstrating that the two step nested multiplex amplification generates single molecular species.

In some embodiments, a target nucleic acid sequence is present in a very low copy number in a sample. The target nucleic acid can comprise a very small portion of the overall sample and/or there can be other nucleic acids present. For example, in PCR-based pathogen detection applications, the pathogens of interest may be present at very low copy number in a sample, and the sample may be contaminated with a large excess of other nucleic acids, illustratively human nucleic acid (e.g., blood) or other microbial genomes (e.g., stool) and may result in a complex nucleic acid mixture. In conventional single-stage PCR detection systems, the single-stage PCR amplification from this complex nucleic acid mixture often results in multiple non-specific products in addition to the desired specific amplicon. Therefore conventional single-stage PCR detection systems often require a second detection mechanism or "filter", in addition to the basic single-stage PCR to isolate the correct amplicon and/or to confirm the identification of the correct amplicon. This filter can include a size exclusion step (e.g., agarose or acrylamide gel) to identify the target amplicon, a probe based detection method (e.g., using a hydrolysis probe or two hybridization probes) or sequence capture method using sequence capture to a surface (GenMark Diagnostics, Inc., Carlsbad, Calif.) or to a bead (Luminex Corporation, Austin, Tex.) that can be sorted.

In some embodiments, because two-step PCR generates amplicons that are essentially homogeneous, the second detection mechanism or "filter" can be omitted and the amplicons generated in the second-stage PCR can be directly sequenced. Thus the amplicons generated by the second-stage PCR can be directly sequenced by any means known in the art.

Illustratively, it should be possible to sequence the population by tethering a portion of the amplicon to the well, illustratively by covalently linking a second-stage primer or the amplicon to the bottom of the well, and then using a next generation sequencing method that may be based on the NGS technologies of Ion Torrent, 454, Illumina or ABI (SoLiD), or other sequencing methods, as are known in the art. Unlike other systems, this subsequent sequencing may be accomplished automatically, within one or more of the second-stage wells.

Example 1

Figure 2A:
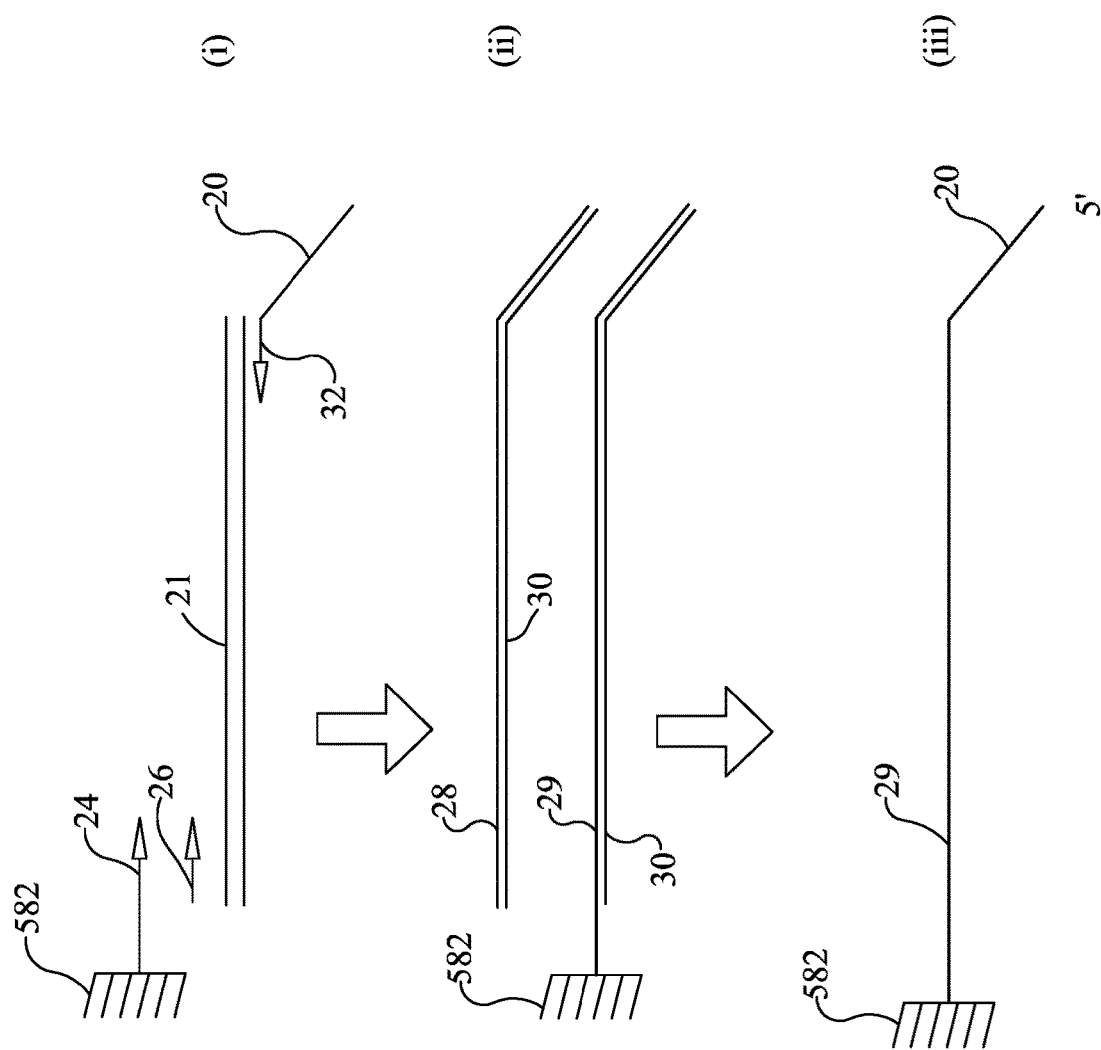
FIGS. 2A-B illustrate steps used for amplification and sequencing in a single sample well.

In this example, one strand of the amplicon is tethered to the bottom of the well (FIG. 2A) prior to sequencing. In one illustrative example, one way to provide tethered amplicon would be to synthesize one of the oligonucleotides (illustratively the forward primer) in two forms, one with the normal 5' OH and the other with a 5' extension that has a chemical moiety provided on the 5' end that allows it to be cross linked to the well surface. There are a variety of chemistries that are known in the art for this purpose. This would provide some of the forward primer tethered to the reaction well and some of the forward primer free in solution. It is understood that the forward primer free in solution is provided to improve the kinetics of the amplification reaction. One illustrative way to load the second-stage array 581 would be to spot the array twice, illustratively using a device such as that described in WO 2013/158740 and U.S. Ser. No. 14/395,002, herein incorporated by reference. Illustratively, the first time array 581 is spotted, the chemically modified primers 24 are added into each well 582 of array 581. The chemically modified primers 24 are then cross-linked to the well 582 and subsequently the coupling reaction may be quenched to prevent further cross-linking of molecules to the array. The array 581 may be dried and then spotted again with reverse primers 32, and optionally other PCR components. Optionally, the unmodified forward primers 26 may be spotted to provide increased primer concentrations to improve the kinetics of the PCR amplification. However, this method for spotting array 581 is illustrative only, and it is understood that the chemically modified primers 24 (as shown in FIG. 2A), unmodified forward primers 26, and reverse primers 32 may be spotted at one time, or in any order. In other embodiments, the chemically modified primer 24 may be spotted together with or prior to spotting the reverse primer 32, and the unmodified forward primer 26 may be omitted. Illustratively, the reverse primer 32 may have a 5' extension sequence 20 that is the same for all reverse primers in the array 581. This "universal primer" is provided to be used later during the sequencing reaction. In the illustrative embodiment with some forward primer provided free in solution, most of the PCR reaction will occur in solution but a fraction of the amplicons 28 will be in the form of a tethered amplicon 29 that is tethered to the well 582 in array 581 (see FIG. 2A). Many of the examples herein describe tethering one or more primers to sample wells or spots on an array. However, it is understood that when tethering is discussed, this may include tethering to any solid surface, including beads, that can be moved to sequencing locations.

Example 2

Figure 3:
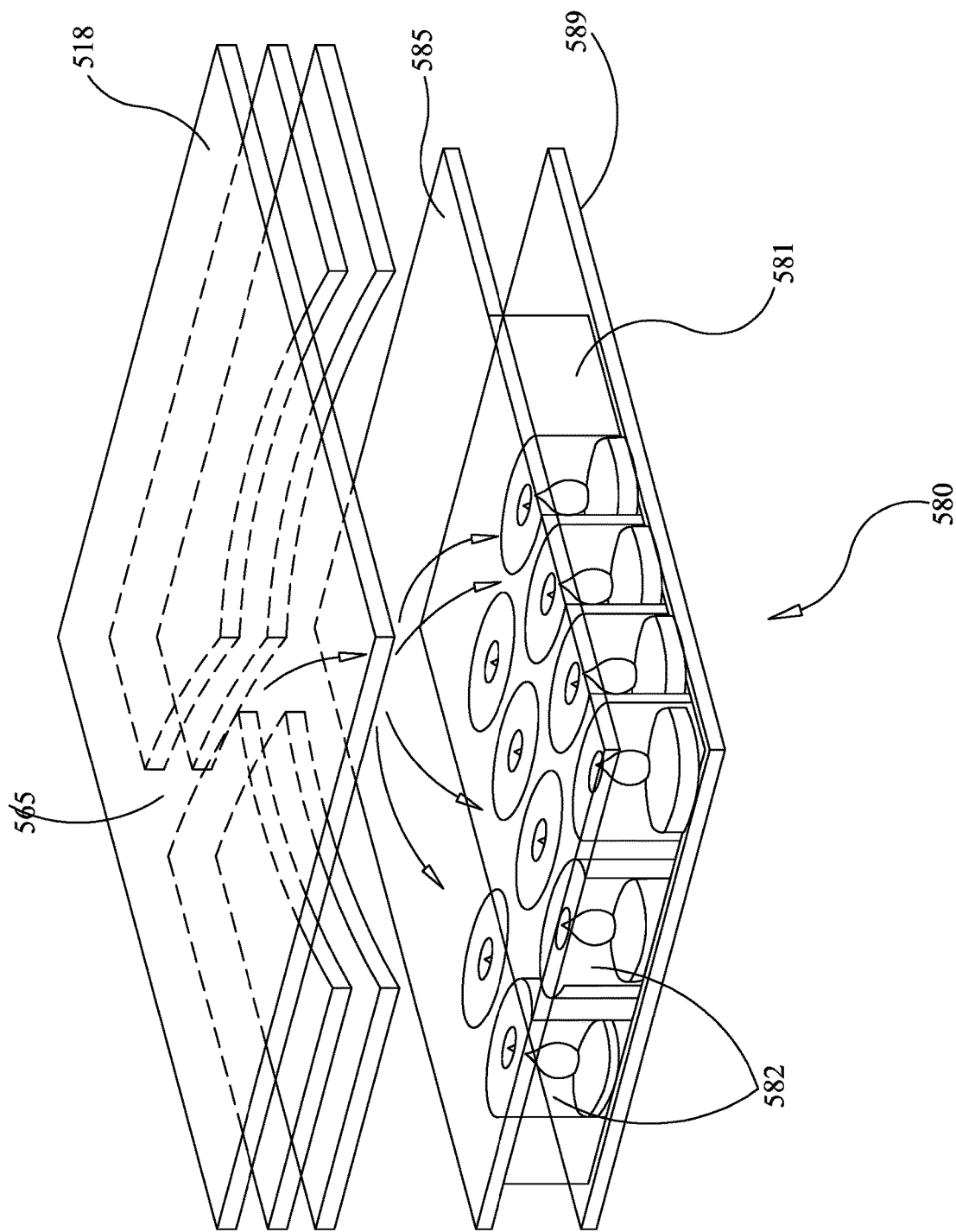
FIG. 3 is a partially exploded view of an illustrative second-stage of the pouch of FIG. 1, configured for sequencing subsequent to amplification.

In this example, an illustrative example of a geometry of the second-stage PCR array 580 as a sequencing chip is described. FIG. 3 shows a partially exploded cross-sectional view of illustrative array 581. In this illustrative embodiment, a silicon layer 589 is built onto the bottom of array 581, illustratively replacing second layer 587 (not shown), as discussed in U.S. Pat. No. 8,895,295, and forming a bottom surface in each of wells 582.

As mentioned above, illustrative ways of filling and sealing the high density array 581 without cross-contamination are discussed in U.S. Pat. No. 8,895,295, already incorporated by reference. In one illustrative embodiment, shown in FIG. 3, a pierced layer 585 is provided, similar to pierced layer 585 of U.S. Pat. No. 8,895,295. Pierced layer 585 allows fluid to pass into each well 582 in the presence of a force, but the piercings are small enough to substantially prevent fluid from passing in the absence of the force. However, it is understood that a chemical mechanism for keeping the primers in place during rehydration may be as or more desirable than the pierced layer in the present embodiment, to provide less interference in the subsequent sequencing step. In one embodiment employing a chemical mechanism, the "solution phase" forward primers 26 and reverse primers 32 may be combined with a solution of molten low melt agarose, for example UltraPure™ Low Melting Point Agarose (Life Technologies), before spotting so that they do not wash out of the array when it is first flooded, although other materials for the chemical mechanism are known in the art, some of which are discussed in U.S. Pat. No. 8,895,295. After flooding second-stage array 581, the wells 582 in array 581 are sealed shut by inflating a bladder in the instrument, discussed in U.S. Pat. No. 8,895,295, and pushing against film 518, which is the same or similar to layer 518, as described in U.S. Pat. No. 8,895,295. In embodiments using low melt agarose, once the wells 582 are sealed, heating of the array releases forward primer 26 and reverse primer 22 into solution. Array 581 may be made largely of silicon, or may be provided with silicon layer 589, with the remainder of materials similar to array 581, as discussed in U.S. Pat. No. 8,895,295, or may be made of other materials and is configured such that liquid flowing across array 581 is able to enter the wells 582 and introduce new chemicals or wash out previous chemicals. It may be desirable to provide array 581 with a depth of from about 50 µm to about 500 µm, but other sizes may be appropriate, depending on sequence method and configuration.

Referring to FIG. 1, second-stage reaction zone 580 is provided with two ports, channel 565 and channel 567, each of which may be sealed by pressure or other means. Channel 565 is provided for receiving fluid from blister 566, which is shown connected to multiple entry channels. Injection channel 515k may contain materials for sequencing, or may have a valve or sealable port, allowing connection to an external source for the materials needed for sequencing. Similarly injection channel 515l may receive the waste materials from sequencing or may be provided with a valve or sealable port for connection to a separate waste receptacle. Thus, in this illustrative embodiment, liquid flows from injection channel 515k, through channel 565, across all wells 582 of array 581 and outlet channel 567, to waste reservoir 515l. It is understood that, as fluid is moved into second-stage amplification zone 580, outlet channel may remain sealed. This will form a bubble of fluid over array 581, and agitation can create a homogenized fluid above the array. Synchronized opening and closing of channels 565 and 567 can control flow of fluid across array 581.

Figure 2B:
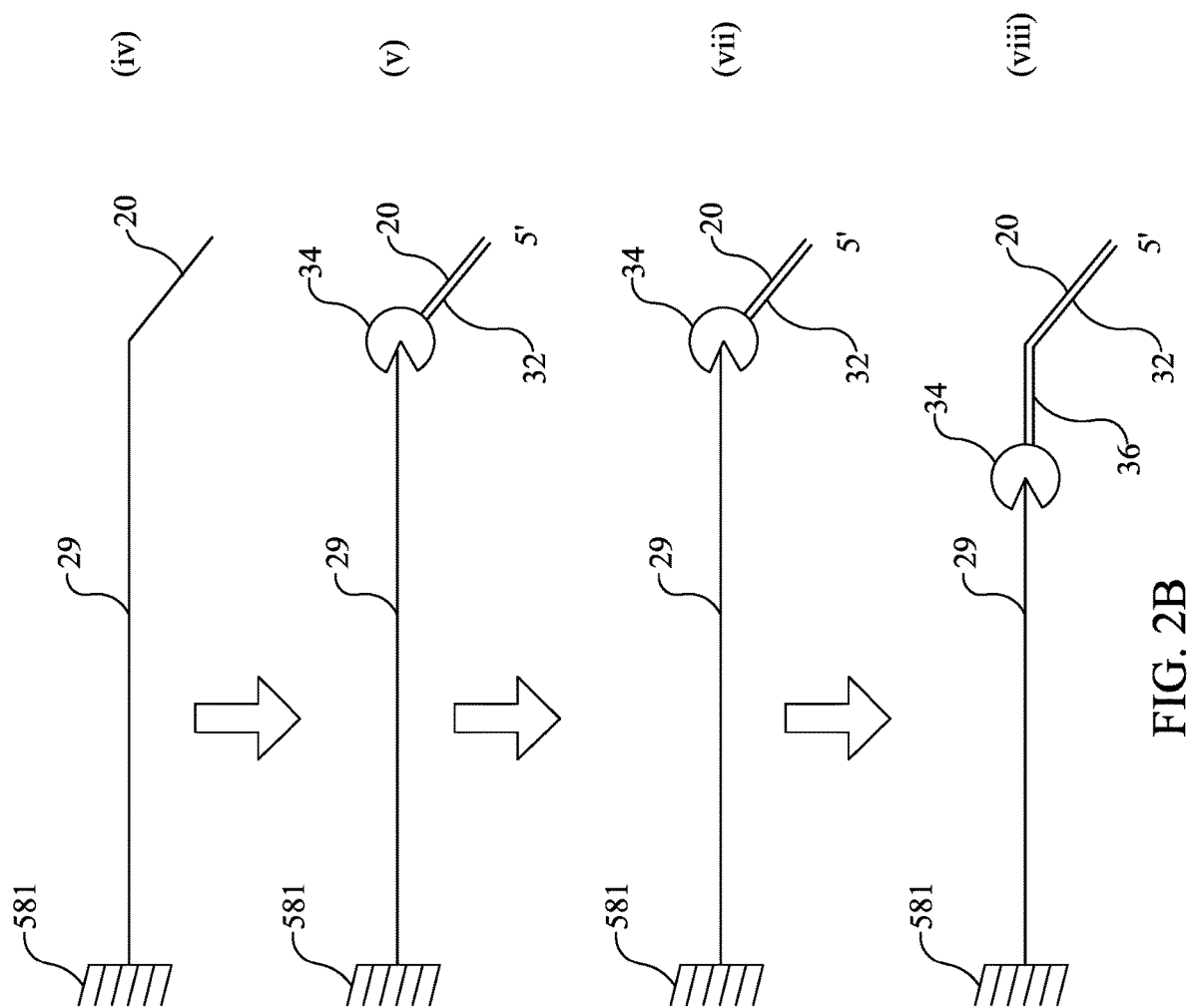

Subsequent to amplification of first stage amplicon 21 (FIG. 2A (i) and (ii)), sequencing illustratively may be performed by the following steps:

1) Denaturing the tethered amplicon 29, illustratively by heating, and washing the unbound strand 30 from the array (FIG. 2A (ii) and FIG. 2A (iii)). It is understood that this will also wash out all unbound amplicon 28.
2) Annealing sequencing primer 32 to universal tail 20 and providing a DNA polymerase 34 to form an initiation complex. Washing out unbound sequencing primer and unbound DNA polymerase (FIG. 2B (iv) and (v))
3) Sequencing. Sequencing may be performed by synthesis as the DNA polymerase moves along the bound strand 29 and amplifies the sequence of the bound strand 29. Each of the nucleotides A, T, C, and G are individually provided and incorporation of the individual dNTPs is measured, thereby revealing the nucleotide sequence of bound strand 29. The incorporation of individual dNTPs can be measured by methods know in the art (e.g., proton generation (as with Ion Torrent), fluorescence or chemiluminescence (as with Roche 454), or any other signal as is appropriate for the sequencing method). Array 581 is washed, and this is repeated until the sequence has been generated (FIG. 2B (vi) and (vii)).

In an alternative embodiment, PCR may be performed in pouch 510 with real-time curves and/or a melt, and then each well 582 is sealed and second-stage amplification zone 580 of pouch 510 is removed to a second instrument for sequencing. Tethering the forward primer, as discussed above, may be one way to prevent well-to-well contamination, although other ways may be possible, illustratively by sealing wells 582. Thus, tethering may be optional, depending on the sequencing method used.

It is understood that other sequencing methods may be used in such a system. One such illustrative method would not require linking the amplicon to the well and would rather use a single molecule sequencing method (Oxford Nanopore, see Wolna A H, et al. Electrical Current Signatures of DNA Base Modifications in Single Molecules Immobilized in the α-Hemolysin Ion Channel. Isr J Chem. 2013 Jun. 1; 53(6-7):417-430. PubMed PMID:24052667; PubMed Central PMCID: PMC3773884). In such an alternate embodiment, the array well 582 may be connected to or integrated with a chamber with a single channel and the population of second-stage amplicons in the well 582 is read one base at a time as the amplicon is translocated through the channel. This connection to the chamber could be built into pouch 510 or it could be made after the second-stage PCR run is completed (as long as the amplicons are kept segregated into their individual wells). Illustratively, after amplification, one side of the array 581 is sealed onto a layer of film that has a single protein nanopore channel disposed over each well. On the other side of the channel is additional fluid so that an electric current can be applied between the well 582 and the additional fluid and through the protein nanopore channel Sequencing can then be performed on the amplicons as they migrate through the protein nanopore channels as per Oxford Nanopore, or by similar methods. Illustratively, Oxford Nanopore uses the protein α-hemolysin as the protein nanopore channel. The protein nanopore is disposed in a lipid bilayer and has a sufficiently sized opening to translocate a single stranded DNA molecule through the opening. As the single-stranded DNA molecule traverses the nanopore, protons and other ions that otherwise flow across the nanopore are impeded and consequently current flow across the nanopore is altered. In the Oxford Nanopore system, the identity (A, T, G, or C) of individual bases of the single-stranded DNA molecule can be individually discerned by this alteration in current flow. Thus, by measuring changes in electrical potential caused by current alterations corresponding to individual base pairs, the sequence of the individual nucleotides within the single-stranded DNA molecule can be ascertained. (See Maglia, Giovanni, et al. "Analysis of single nucleic acid molecules with protein nanopores." Methods in enzymology 475 (2010): 591-623 and Clarke, James, et al. "Continuous base identification for single-molecule nanopore DNA sequencing." Nature Nanotechnology 4.4 (2009): 265-270.) However, it is understood that the Oxford Nanopore system is illustrative and that other sequencing configurations are contemplated. In another version, similar to the method developed by Pacific Biosciences of Menlo Park, Calif., a sequencing well comprises zero-mode waveguides on a bottom surface that create a small light detection volume. Each zero-mode waveguide is illuminated from below by an excitation beam and the zero-mode waveguide prevents the wavelength of light from efficiently passing through the waveguide thereby allowing attenuated light from the excitation beam to penetrate the lower 20-30 nm of each zero-mode waveguide. A complex of the amplicon and a DNA polymerase complex is then tethered to the bottom of the zero-mode waveguide. Phospho-linked nucleotides are then added to the well. Each of the four nucleotides can be labelled with a different colored fluorophore. As the DNA polymerase complex amplifies the amplicon, the individual phospho-linked nucleotides are incorporated into the nascent strand and the fluorescent color of each individual phosphor-linked nucleotide can be detected in sequential order to determine the nucleotide sequence of the amplicon. Since there are multiple polymerases per original well, the incorporation of nucleotides into each strand held by each polymerase should be synchronized for best results.

In one illustrative example for demonstrating that a single molecular species results from two-step nested multiplex PCR, second-stage amplicons from a FilmArray run have been sequenced. As part of an investigation of false positive test results in the FilmArray BCID Panel (BioFire Diagnostics), a mixture of organisms including *Candida glabrata*, *Neisseria meningitidis*, *Escherichia coli*, and *Streptococcus mitis*, was tested using a commercial FilmArray BCID Panel and experimental software. A weak false positive result with very late Cps, indicative of poor amplification, was detected in the *Candida krusei* second-stage wells.

Amplicon from each of these positive second-stage wells was extracted from the pouches by piercing of each of the wells on the second-stage array with an insulin syringe and withdrawing the solution containing the amplicon. The amplicon was then amplified in a CFX instrument (Bio-Rad) for an additional 20 cycles using the same *Candida krusei* inner primers as used in the second-stage of the BCID Panel. This further amplified material was then sequenced by Sanger sequencing on an ABI instrument. Readable sequence could be obtained using both the forward and reverse primers with Phred quality scores above 20 for 51 nucleotides (forward primer) and 75 nucleotides (reverse primer). Table 1 shows the results of sequence comparison using the BLAST algorithm of the contiguous sequence (made from the overlapping regions of the forward and reverse sequences) against the GenBank database (National Center for Biotechnology Information).

TABLE 1

| Description | Max Score | Total Score | Query cover | E value | Ident | Accession |
|---|---|---|---|---|---|---|
| *Streptococcus mitis* strain SVGS_061, complete genome | 194 | 194 | 99% | 3e−46 | 97% | CP014326.1 |
| *Streptococcus pneumoniae* ST556, complete genome | 194 | 194 | 99% | 3e−46 | 97% | CP003357.2 |
| *Streptococcus pneumoniae* genome assembly S_pneumo_A66_v1, chromosome: 1 | 194 | 194 | 99% | 3e−46 | 97% | LN847353.1 |
| *Streptococcus pneumoniae* genome assembly NCTC7465, chromosome: 1 | 194 | 194 | 99% | 3e−46 | 97% | LN831051.1 |
| *Streptococcus pneumoniae* strain NT_110_58, complete genome | 194 | 194 | 99% | 3e−46 | 97% | CP007593.1 |
| *Streptococcus pneumoniae* A026 genome | 194 | 194 | 99% | 3e−46 | 97% | CP006844.1 |
| *Streptococcus pneumoniae* SPN994038 draft genome | 194 | 194 | 99% | 3e−46 | 97% | PQ312041.2 |

These data show that the *C. krusei* assay in the second-stage of the BCID Panel is specifically amplifying a region of the *Streptococcus mitis* genome. This demonstrates that good sequence data can be obtained from the two-step nested multiplex PCR in the BCID Panel even when the PCR that produced the sequence had a very late Cp, indicating that the amplicon was not abundant.

Example 3

Figure 4:
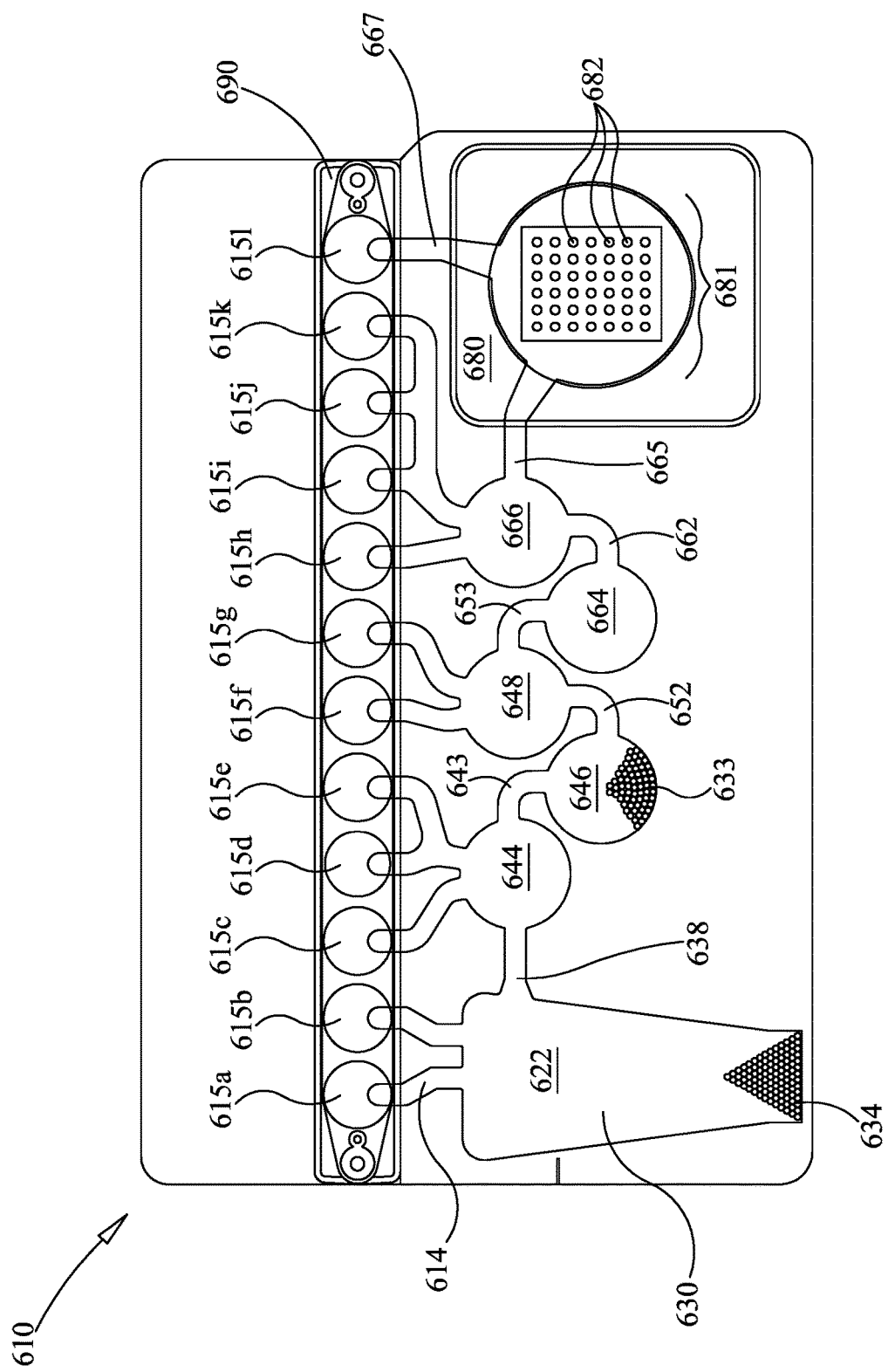
FIG. 4 is similar to FIG. 1, but showing a different embodiment for the second-stage array.

In this example, illustrative embodiments of nucleotide sequencing in a two-step PCR system are described. Referring now to FIG. 4, FIG. 4 is similar to FIG. 1, with like reference numerals indicating similar components. In this embodiment, array 580 with wells 582 are replaced by a microarray 680 with spots 682 (often referred to as features). Spots 682 are areas of the array that have at least one oligonucleotide deposited thereon. While having one homogenous group of oligonucleotides spotted per spot 682 is used illustratively herein, it is understood that each spot 682 may have both members of a primer pair, or may have a set of nested oligonucleotides spotted thereon, and other configurations are possible. Thus, it is understood that each spot 682 has one set of oligonucleotides spotted thereon, where each set is one or more oligonucleotide species, and the set is specific for a target.

In one illustrative embodiment, one oligonucleotide species is spotted in each spot 682, which is used to extend one end of an amplicon, and a plurality of spots 682 each has a different oligonucleotide species spotted thereon. It is understood that each spot 682 of array 680 may have a different species, or there may be replicate (illustratively duplicate or triplicate) spots, or any combination thereof.

In another illustrative embodiment that will be discussed in more detail below, two members of a primer pair are spotted at the same spot 682 on the array, allowing for bridge PCR at that spot, so that the whole spot 682 becomes covered with amplicon that is anchored by one or the other end. Prior art next generation sequencers that use bridge PCR randomly deposits primers across the whole flow cell, permitting amplification of any single member of the library that has been deposited on the array. By spotting both members of a primer pair in a single spot 682, a sequence will be obtained from that spot 682 only if the target sequence is present. Thus, obtaining a sequence from that spot not only provides the sequence, but can also provide a positive call for that target.

Illustratively, the substrate material for array 680 may be glass. Many microarrays are made on a glass surface, illustratively because: (1) the chemistry for coupling oligonucleotides to glass at high loading density is well understood; (2) the flatness and lack of stretching means that array printers can place small spots very close to each other; and (3) glass has relatively low auto-fluorescence, so that the signal-to-noise ratio for a fluorescent dye on the array is easier to detect. Integration of a glass array into the pouch 610 may require putting a hard frame around array 680 or around pouch 610, to reduce breakage of a glass array 680.

However, it is understood that other materials may be used for array 680. Methods are known in the art for attaching oligonucleotides to plastic. In some embodiments, a plastic array can have one or more of the following: (1) plastic bonds to the other plastic components easily and can be more readily integrated into pouch 610, (2) a flexible plastic may be used, so that array 681 is less breakable if pouch 610 is stressed. A plastic microarray may work well in pouch 610 because (a) one can make relatively large spots so the signal will relatively large and the accuracy of spotting is not critical (256 spots on a 1 square cm array area=square spots of 0.39 $mm^2$). A spot of this size is quite large by microarray standards. By comparison the commercial FilmArray wells are circles of 1.98 $mm^2$ area (the wells are 1.59 mm in diameter). Larger spots will generate larger signals which means that the camera for imaging fluorescent nucleotide incorporation will need fewer sensing elements or the silicon chip used to sense pH changes will require fewer transistors, which will make both devices less expensive to manufacture, and (b) plastics are known that have low auto-fluorescence and can still bind oligonucleotides at a relatively high density. It is understood that an array of 512 spots or fewer, or 256 spots or fewer, or any number of spots are contemplated.

It is understood that the illustrative arrays described herein can have the oligonucleotides tethered at the 5' end to the well 682. In that sense they are different from many other arrays known in the art, e.g. Affymetrix arrays, that have the oligonucleotide attached by its 3' end to the substrate (e.g., the well). Accordingly, Affymetrix arrays can only be used for hybridization, not for extension as a primer in an amplification reaction as in the illustrative arrays.

A DNA polymerase with a 3' to 5' exonuclease activity (for example T4 DNA polymerase, T7 DNA polymerase or Vent DNA polymerase), in addition to acting as a DNA polymerase can perform the following additional activities (in the presence of dNTPs): (1) remove bases from a 3' overhang of a double-stranded DNA and (2) degrade single-stranded DNA to nucleotides. (See New England BioLabs, New England. "New England BioLabs catalog and technical reference." Beverly, Mass.: New England Biolabs (2014) and BEBENEK, K. et al. (1989) Nucl. Acids Res. 17, 5408, herein incorporated by reference.) In some embodiments, these 3' to 5' exonuclease DNA polymerases with these additional activities are useful in two-step nested multiplex PCR. In certain commercial embodiments, at the end of first-stage PCR, the reaction mixture is be diluted, illustratively 100 to 250-fold, prior to the nested second-stage reactions, and new inner nested primers are used (primers that are nested within the first-stage primers). This is done to prevent the first-stage PCR primers from continuing to amplify any primer dimers, which avoids a non-specific rising baseline in the amplification curve and a large, broad, melt peak in second-stage PCR. An illustrative treatment a DNA polymerase with 3' to 5' exonuclease activity (e.g., an exo+ DNA polymerase) in the presence of dNTPs will degrade the first-stage primers that have not been incorporated into double-stranded amplicon. The correct amplicons, non-specific amplicons and primer dimers are all double-stranded, so they should remain intact. Without the first-stage PCR primers, the primer dimers present from first-stage PCR should not amplify in second-stage PCR, thus enabling a smaller dilution (or no dilution) between first-stage PCR and second-stage PCR, which means that fewer cycles will be needed to get a second-stage amplicon to appear above background (have an earlier Cp in the second stage reaction).

In addition, the exo+ DNA polymerase treatment will degrade segments of high complexity genomes (such as the human genomic DNA, human mRNA converted to cDNA (when an RT-PCR step is used), as well as non-amplified pathogens and contamination that may be present) that are in low copy number. This may happen because standard PCR cycling conditions (in particular the annealing step) may be fast enough to prevent low copy high complexity DNA from reannealing, and thus will be degraded by the exo+ activity, although some sequences that are present in higher copy numbers may reanneal. An advantage of using exonuclease at this step is that it reduces the sequence complexity of the DNA that enters the second-stage PCR reaction. This can result in less non-specific amplification in second-stage PCR that could be detected by a double-stranded DNA binding dye, such as LCGreen. Thus, it can be possible to add additional cycles to second-stage PCR with less signal interference from mis-amplification.

In one illustrative example, in pouch 610, two successive dilutions of about 10 to 15-fold each, equaling 100 to 225-fold total dilution, are made using components from injection channels 616h, 615i, and/or 615j. As an alternative to performing this level of dilution, in one illustrative embodiment, a small amount of the exo+ polymerase can be added directly to the first-stage PCR at the end of cycling, illustratively from injection channel 615h. This may require a longer digestion because of the large number of primers present in the highly-multiplexed first-stage PCR. It is understood that most of these primers are still single stranded, as only a few targets usually amplify in any single run. However, any advantage in reduced speed in second-stage PCR may be lost by the time it takes to perform this large digestion. Thus, it may be desirable to perform a single dilution, illustratively 10 to 15 fold, prior to or simultaneously with the exo+ digestion. Illustratively, if the exo+ enzyme is T4 or T7, the mixture may be incubated at 37 to 42° C. respectively for a time sufficient to allow the first-stage PCR primers to be degraded. At the end of this step, the mixture may be heated to 80 to 90° C. for a time long enough to inactivate the exo+ enzyme. This mixture can then be flooded across the second-stage array 681.

In some embodiments, Vent DNA polymerase with 3' to 5' exonuclease is used and steps must be taken to prevent inactivation of the second-stage PCR primers by the Vent Polymerase. Vent Polymerase is not thermolabile so it cannot be inactivated by heat before carrying out the second-stage PCR amplification. To prevent inactivation of the second-stage PCR primers by the 3' to 5' exonuclease activity of the Vent Polymerase, the concentration of Vent polymerase may be titered to a level low enough that it will not degrade the second-stage primers (See Barnes WM. PNAS USA. 1994 Mar. 15; 91(6):2216-20. PMID: 8134376, which describes the use of a mixture of KlenTaq polymerase and Vent DNA polymerase where the KlenTaq comprises a major component of the mixture and Vent DNA polymerase is a minor component of the mixture). It is also possible to use second-stage primers that contain a few bases with phosphorthioate bonds at the 3' ends of the oligonucleotide because these bases are resistant to digestion by the exo+ activity of 3' to 5' exonuclease DNA polymerases (See Chrisey, L. A. (1991) Antisense, Research and Development 1 (1), 65-113; Spitzer, S.; Eckstein, F. (1988) Nucl. Acids. Res. 16 (24), 11691-11704. Connolly, B. A.; Potter, B. V. L.; Eckstein, F.; Pingoud, A.; Grotjahn, L. (1984) Biochemistry 23, 3443-3453; Stein, C. A.; Pal, R.; Devico, A. L.; Hoke, G.; Mumbauer, S.; Kinstler, O.; Sarngadharan, M. G.; Letsinger, R. L. (1991) Biochemistry 30 (9), 2439-2444. Sayers, J. R.; Olsen, D. B.; Eckstein, F. (1989) Nucl. Acids Res. 17 (22) 9495. Manson, J.; Brown, T.; Duff, G. (1990) Lymphokine Research 9 (1), 35-42. Woolf, T. M.; Jennings, C. B. G.; Rebagliati, M.; Melton, D. A. (1990) Nucl. Acids Res. 18 (7), 1763-1769. Leiter, J. M. E.; Agrawal, S.; Palese, P.; Zamecnik, P. C. (1990) Proc. Natl. Acad. Sci. USA 87 (9), 3430-3434. Reed, J. C.; Stein, C.; Subasinghe, C.; Haldar, S.; Croce, C. M.; Yum, S.; Cohen, J. (1990) Cancer Research 50 (20), 6565-6570; Iyer, R. P.; Egan, W.; Regan, J. B.; Beaucage, S. L. (1990) J. Am. Chem Soc. 112, 1254-1255. Iyer, R. P.; Phillips, L. R.; Egan, W.; Regan, J. B.; Beaucage, S. L. (1990) J. Org. Chem. 55, 4693-4699; Dagle, J. M.; Weeks, D. L.; Walder, J. A. (1991) Antisense, Research and Development 1 (1), 11-20. Maher, L. J.; Dolnick, B. J. (1988) Nucl. Acids Res. 16, 3341-3358. Walkder, R. Y.; Walkder, J. A. (1988) Proc. Natl. Acad. Sci. USA 85, 5011-5015, herein incorporated by reference in their entirety).

In addition to reducing the complexity of the second-stage PCR reaction, an exo+ DNA polymerase can also be used to convert longer first-stage PCR amplicons to shorter second-stage PCR amplicons that contain, at their 3' end, the complement of the universal primer sequence used for sequencing.

In some embodiments, certain sequencing methods (e.g., Illumina SBS or Ion Torrent) determine sequencing reads from a single clonal population. It is understood that single nucleotide polymorphisms (SNPs) and insertions and deletions (In/Dels) do not cause ambiguities in these sequences that are determined from a single clonal population. Thus, by comparing sequences across multiple sequence reads, SNPs and/or In/Dels can be located in the population of molecules sequenced, and the specific changes in the SNP and In/Del then can be determined. In other embodiments, where the sequences are not determined from a single clonal population, SNPs and In/Dels may cause ambiguities in the sequences because multiple populations of molecules may contribute to the sequence signal. In some cases, these ambiguities in the sequences can arise for the same reasons in conventional Sanger sequencing. As with that technique it can be possible to determine the nature of the polymorphism, in that an SNP will show up as two different bases at one particular position. Similarly, a one base insertion will be evident as a single sequence up to that base position, and thereafter a mixture of two sequences that are a one base frame shift of each other. It can be possible to deconvolute this information to determine SNPs and In/Dels, just as it has been done for Sanger sequencing.

Returning to FIG. 4, the illustrative array 681 may have between 100 and 1000 spots, but greater or fewer spots are possible, in some cases the spots illustratively may be 2 mm in diameter with the overall array illustratively 25 mm×25 mm. However, this size is illustrative only and any number of spots and any size array are contemplated. In one embodiment, the spots on this array would contain both of a pair of inner primers for a given amplicon generated in first-stage amplification, illustratively in blister 664. The inner primers illustratively each have on their 5' ends an additional sequence that is either complementary to a universal forward or a universal reverse primer (e.g., similar to the common sequencing primers introduced during library production in several different NGS methods). In one embodiment, a barcode primer sequence, as is commonly used in next generation sequencing, may be omitted because the location of the spot encodes the information about the amplicon present in that spot and therefore the identity of the sequence that will be generated in that spot.

After a number of cycles (between about 10 and about 26 cycles depending on the specific assay, wherein 10 cycles may be sufficient for abundant pathogens, and 26 cycles for less abundant targets to get to saturation of product formation in first-stage PCR) this first-stage PCR material is flooded into array 681, as described above. In one example, the sample is transferred to array 681 while hot (so that the PCR products are denatured) and is allowed to cool and hybridize to the primers on array 681. DNA polymerase and dNTPs that enter second-stage amplification zone 680 can extend the tethered oligonucleotides that are hybridized. Illustratively, first-stage amplification product may be diluted or may be used without dilution, as sequencing can be performed after a single round of extension off of the tethered oligonucleotide on the array. After extension, extra material can be pushed back through channel 665 or out through channel 667, and new PCR buffer, enzyme and dNTPs may be introduced from any or all of entry wells 615$i$, 615$j$, and 615$k$. This removes all solution amplicon and the first-stage primers.

Figure 5A:
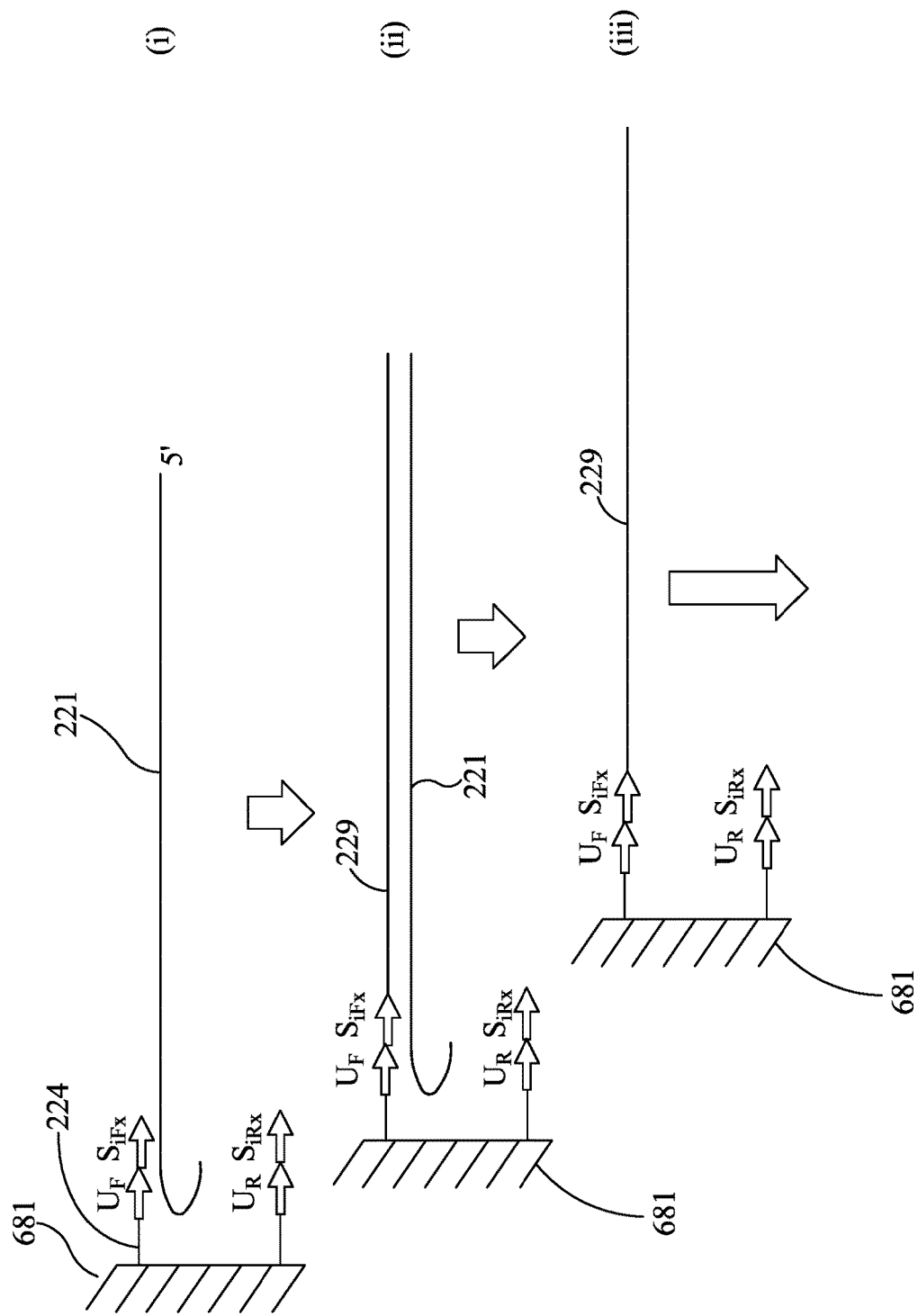
FIGS. 5A-5C are similar to FIGS. 2A-2B, except showing bridge amplification.
Figure 5B:
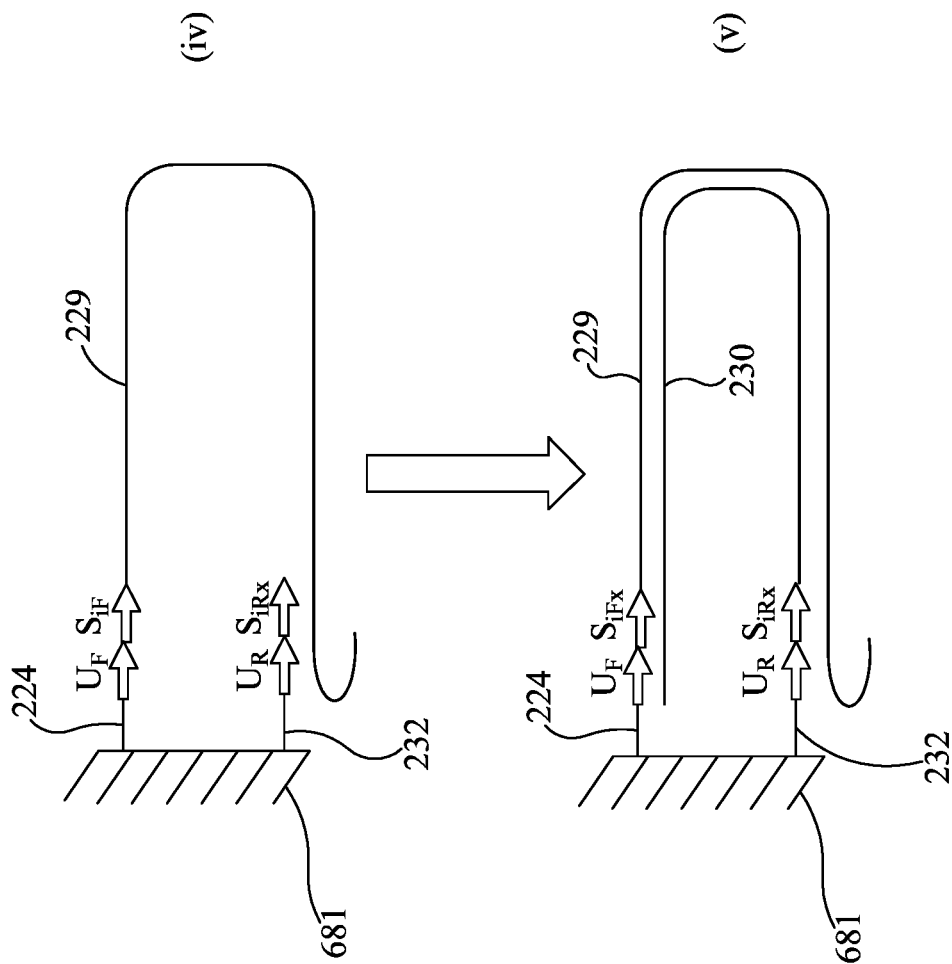
Figure 5C:
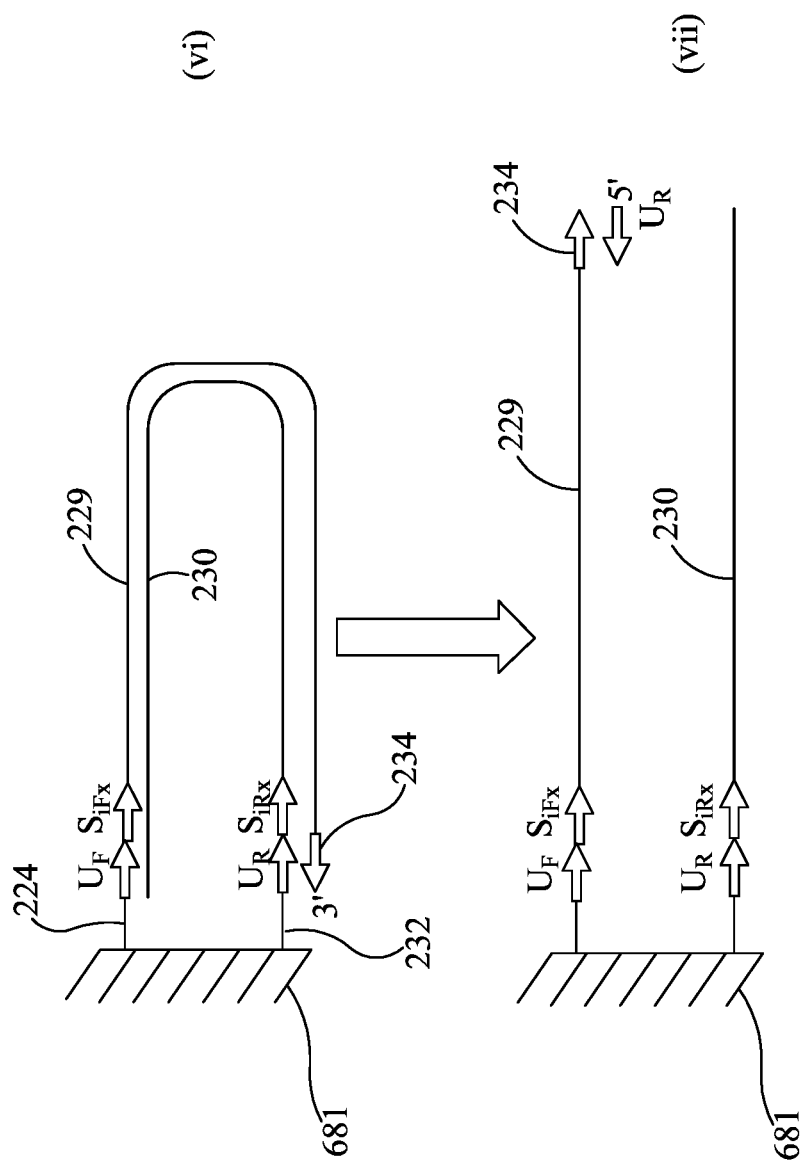

As above, subsequent to amplification in blister 664, amplification may be performed in second-stage amplification zone 680, by moving amplicon 221 into zone 680. Amplification on array 681 using a tethered primer 224 and reverse primer optionally with a sequence complementary to the universal primer as described above. FIGS. 5A-5C show an example using bridge PCR. Amplification of first-stage amplicon 221 first occurs using the $S_{iFx}$ portion of forward primer 224 (FIG. 5A (i)-(iii)) to generate second-stage amplicon 229. The reverse strand 230 may be generated using reverse primer $S_{iRx}$ (FIG. 5B (iv)-(v)). An exo+ DNA polymerase can be used to repair an end 234 of long first-stage amplicon so that it has the $U_R$ primer sequence at its 3' end (FIG. 5C (vi) and (vii)) to be available for sequencing using a $U_R$ primer. Strand 230 includes the complement of the universal primer, $U_F$, at its 3'end so that strand 230 optionally can also be sequences using universal primer $U_F$ using methods similar to those used on the MiSeq or HiSeq (Illumina). Optionally, either or both strands 229, 230 may be sequenced in this embodiment.

Bridge PCR can be done in the presence of a dsDNA binding dye such as LCGreen® (BioFire Diagnostics, LLC), or in the presence of probes or other detecting methods as are known in the art. In one illustrative embodiment, subsequent to bridge PCR, the array is melted and fluorescence from the dsDNA binding dye is used to generate a melting curve that can indicate the presence of specifically amplified products. If the reaction completely failed, then there will be no melting curve and the process may not proceed to the sequencing reaction.

If there is amplicon on the array, then channels 665 and 667 may be used for introducing and removing solutions for sequencing. Then sequencing can be performed by any conventional method, including those described in this application, including by methods such as those described by Illumina (See, e.g., U.S. Pat. Nos. 7,544,794 and 8,946,397, herein incorporated by reference).

It understood that other sequencing mechanisms may also be used. For example an embodiment similar to the 454 pyrosequencing technology may be employed, wherein dNTPs incorporated at a particular spot 682 generate pyrophosphate and additional enzymes convert this to ATP and then to light. This light is detected to reveal the nucleotide sequence. Similarly it may be possible to use Ion Torrent-type technology where the signal generated is a proton and the detection is a pH sensitive transistor element under the array.

Sequencing also could be performed by measuring current changes of molecules flowing through a Nanopore-style channel incorporated in array 681, or array 681 may be moved to the Nanopore instrument. Other sequencing methods are known in the art and are contemplated herein.

In an alternate embodiment, the same pouch 610, as discussed above, may be used, or other vessels for two-step PCR may be employed. However, in this embodiment, only one inner primer of each primer pair is tethered to the array and all of the inner primers are present in the amplification solution in second-stage amplification zone 680. This implementation has the advantage that amplification in solution together with amplification on the array is fast and efficient, but it also has the disadvantage that all of the inner primers are present in the mixture so there will be more non-specific products made and this may result in the products bound to each spot not being a single molecular species. In this implementation, after amplification and melt analysis, the array may be washed of reverse strands and the array becomes like a sequencing library, with the appropriate series of sequencing chemicals flooded over the thin volume of the array and detection as described above. This embodiment is similar to that described with respect to FIG. 1, except that amplification on array 682 is performed in a single reaction mixture.

Figure 6A:
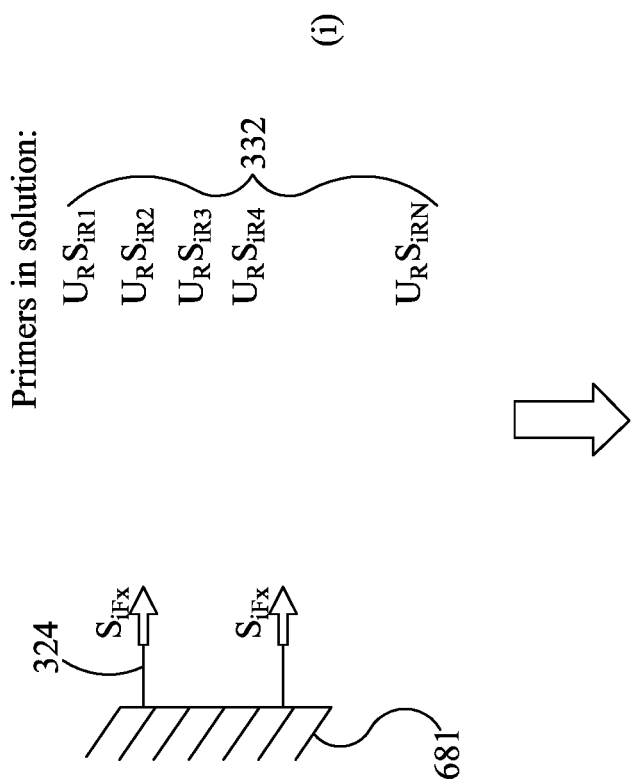
FIGS. 6A-6E are similar to FIGS. 5A-5C, except showing a different embodiment for use with the devices described herein.
Figure 6B:
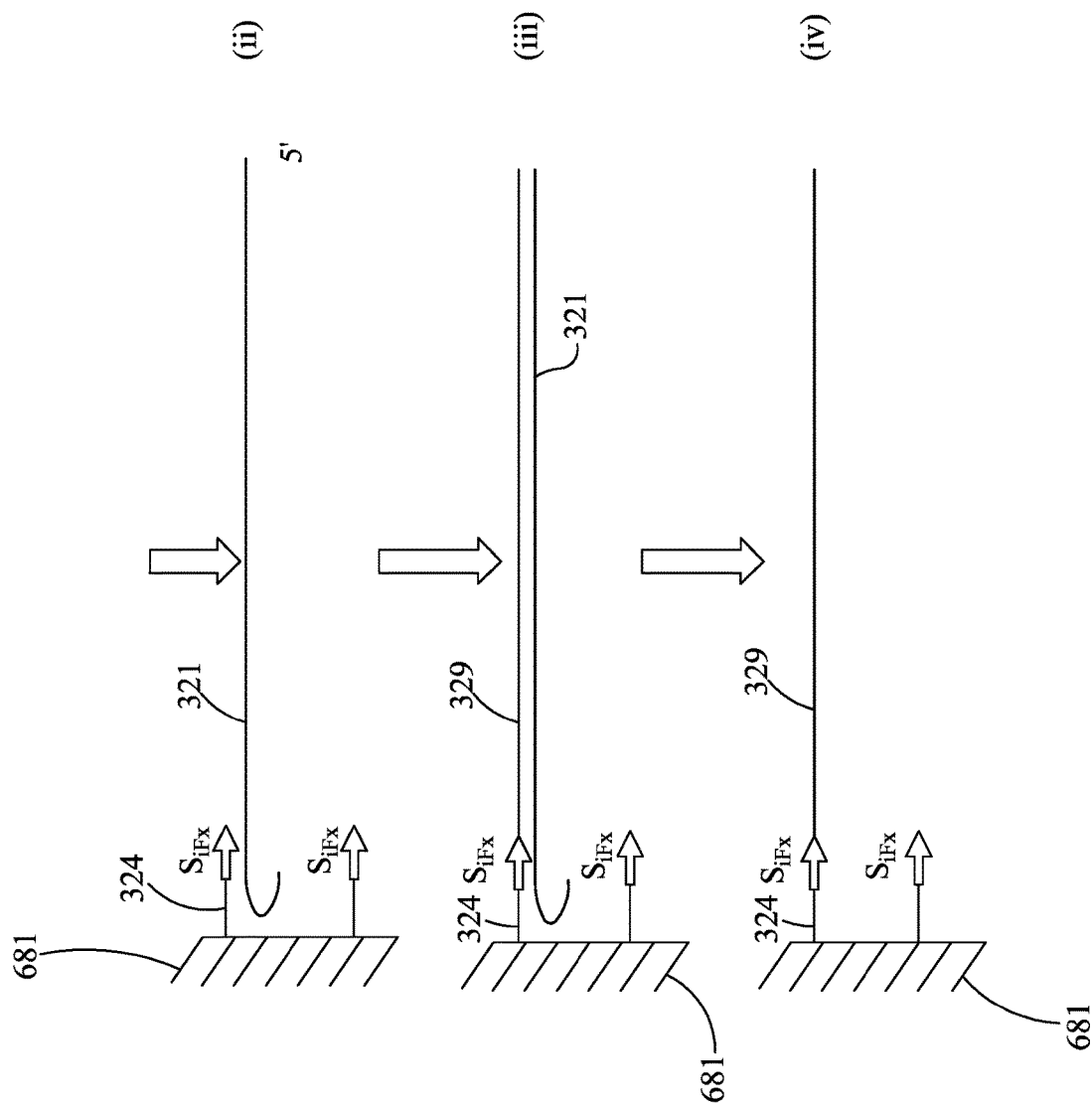

Illustratively, in a similar embodiment, only the specific inner forward primers ($S_{iFx}$ are 324 are tethered to array 681 and only the reverse primers 332 are present in solution (FIG. 6A) for further amplification of first-stage amplicon 321. An advantage is that the multiplex second-stage reaction has roughly half the number of primers present, which should reduce non-specific amplification. However, it also means that the kinetics of amplification are slower since one strand is only made on the array and the other strand is only made in solution (FIGS. 6A-6B (i)-(iv)). In this embodiment, after amplification and optional melt analysis (FIGS. 6A-6B (i)-(iv)), the array is washed of reverse strands (subsequent to denaturation, FIG. 6B (iii)-(iv)) and the array functions as a sequencing library, with the appropriate series of sequencing chemicals flooded over the thin volume of the array and detection, as described above.

Moreover, non-specific amplification with the second-stage reverse primers in solution about array 681 should not interfere with the generation of single molecular species of a second-stage amplicon at each spot 682 on array 681 because the sequence complexity of the material entering this second-stage reaction has been reduced by the enrichment from first-stage PCR. However, it is understood that additional steps can be taken, together or separately, to ensure the single molecular species. In one such step, a 3' to 5' exo+ DNA polymerase can be used, as described above, to reduce the sequence complexity of the input material still further.

Figure 6C:
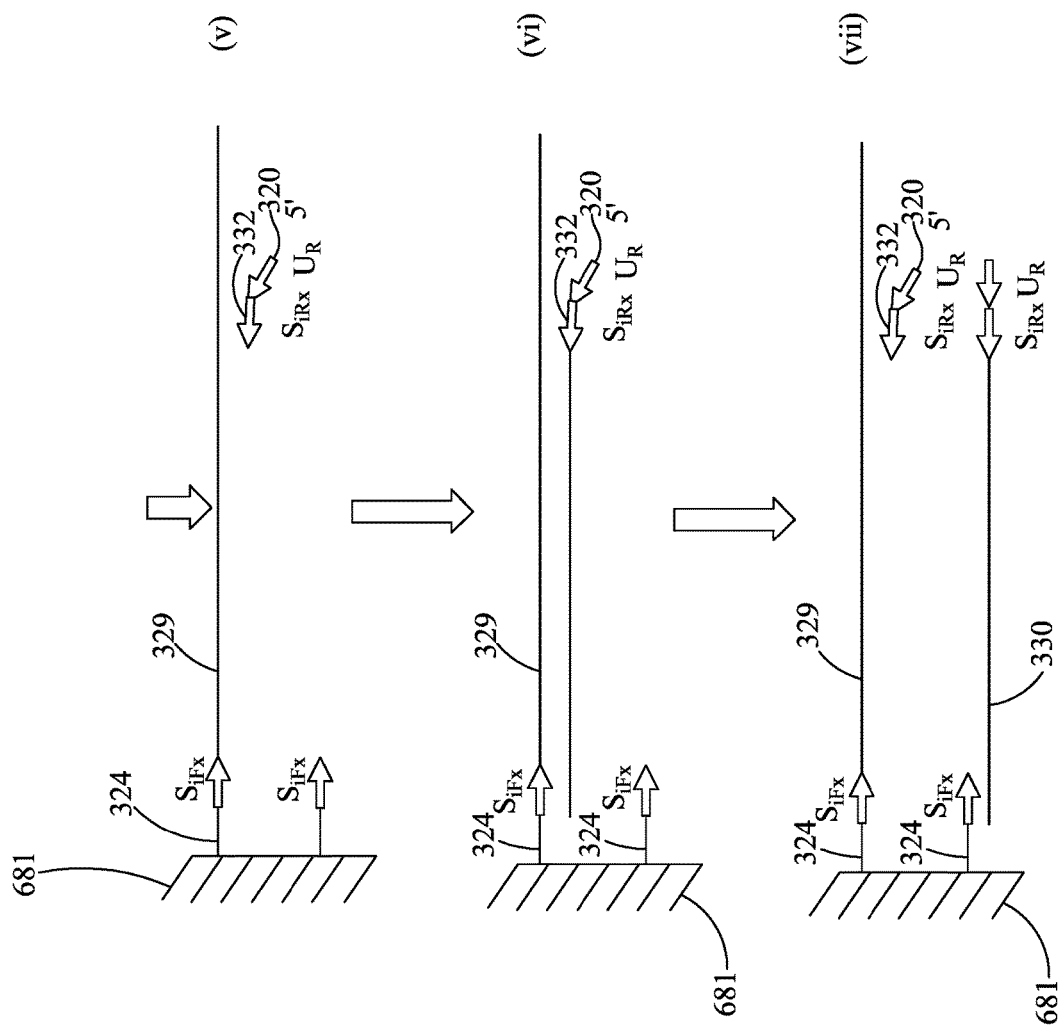
Figure 6D:
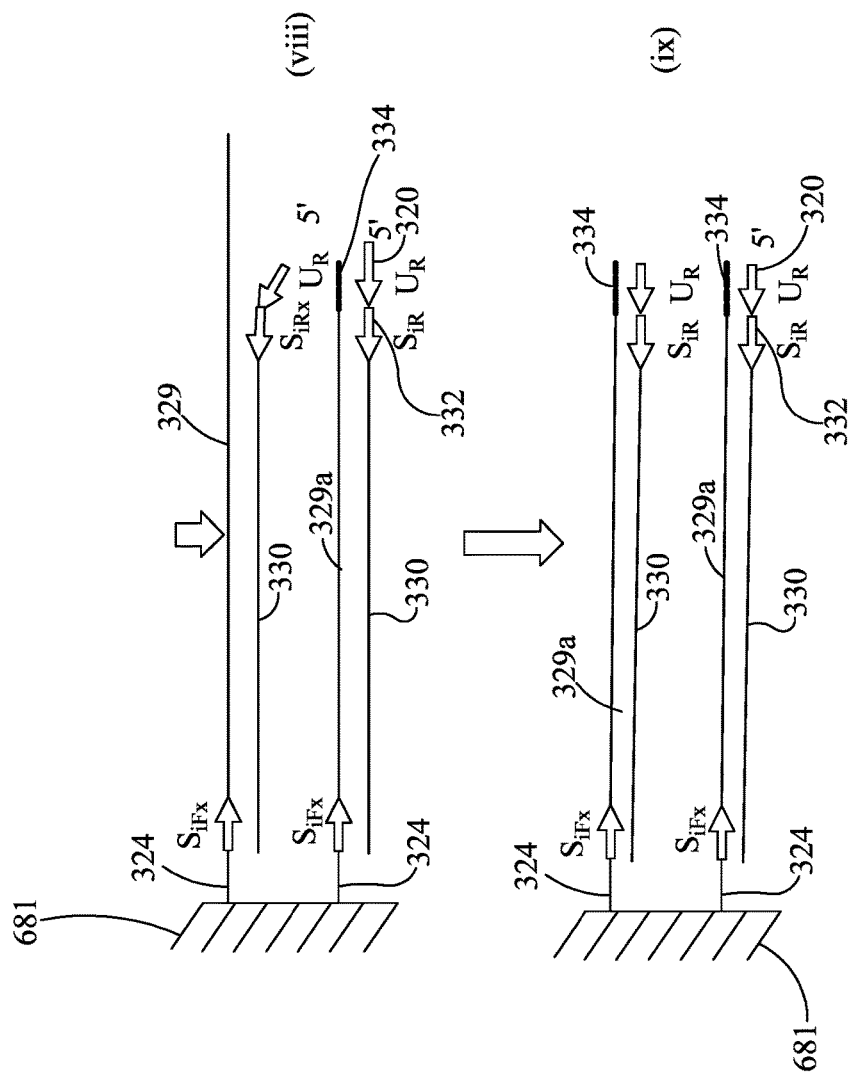
Figure 6E:
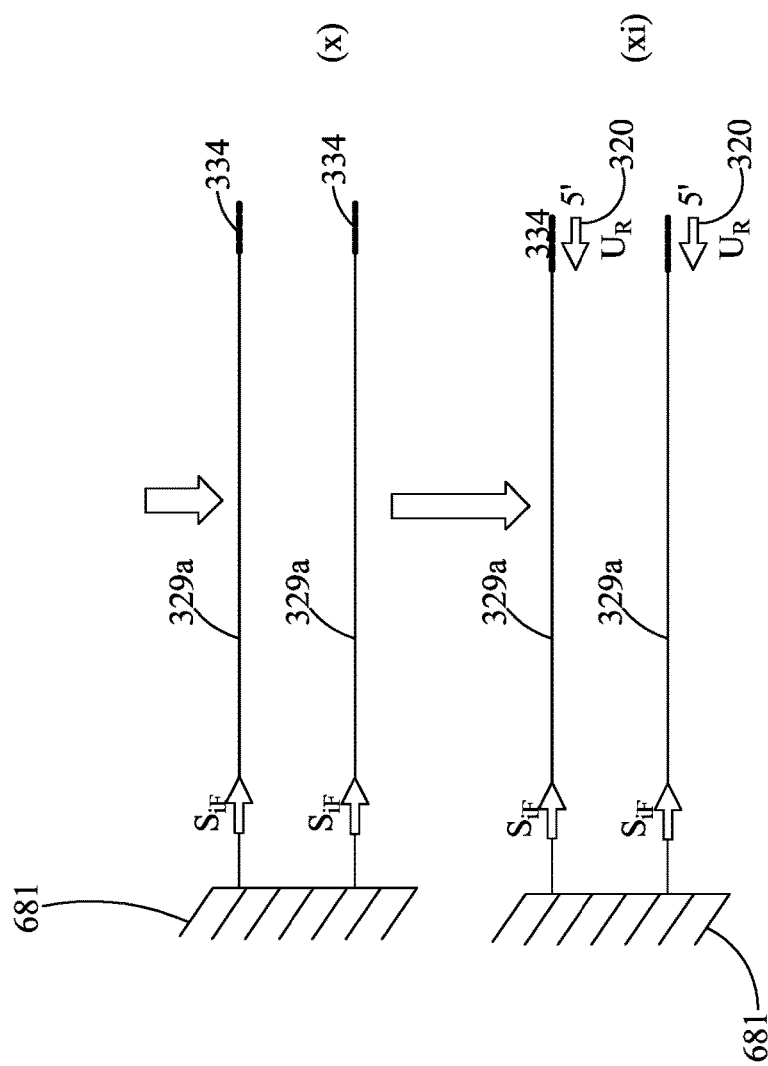

In another illustrative example, the specificity of PCR can be increased using methods such as the Templex method of Genaco Biomedical Products, Inc. (Han J. et al. JCM. 2006 November; 44(11):4157-62. PMID: 17005760). In this illustrative embodiment, the primers 332 present in solution over array 681 include a Universal Reverse sequence 330 that binds on the 5' side of the specific inner primers (best seen in FIGS. 6C-6D). Illustratively, these primers are present at $\frac{1}{10}$th to $\frac{1}{100}$th of the normal concentration present in a standard PCR (standard is 0.4 to 0.8 µM). Creation of primer dimers requires a tri-molecular complex of two primers and DNA polymerase and the rate of formation of this complex is a function of the concentration of the primers. Thus if each of the primers is present at $\frac{1}{10}^{th}$ of the concentration in a standard PCR then the rate of primer dimer formation should be reduced to $\frac{1}{100}^{th}$. In addition to the $U_R S_{iR}$ primers 332 present at low concentration there is an additional primer—the $U_R$ sequence—present at standard primer concentration. After a few cycles (illustratively 3 to 10 cycles) of PCR performed with long extension times so that the low concentration $U_R S_{iR}$ primers have time to hybridize to their targets (FIGS. 6C-6D (v)-(viii)), there is enough complement of the $U_R$ sequence in the nascent amplicons 329. At this point, the $U_R S_{iR}$ primers optionally can be washed away and an exo+ DNA polymerase can be introduced to repair amplicon 329 to generate amplicon 329a, so that it contains a sequence complementary to the universal primer 320 (FIGS. 6D-6E (viii)-(ix)). Then a single $U_R$ primer at the high concentration can be introduced to anneal to this templates (FIG. 6E (xi)) and PCR cycling can proceed with standard annealing and extension times. The net result is that the specificity of the second-stage PCR is increased and thus each feature on the array is more likely to be a single molecular species. Thus, increased specificity is obtained in exchange for a few slower cycles in the early part of PCR.

In a third example, a further extension of the Templex method uses the "self-avoiding molecular recognition system" (SAMRS) and the "artificially expanded genetic information system" (AEGIS) of Benner (Glushakova et al. J. Virol. Methods. 2015 March; 214:60-74. PMID: 25680538), herein incorporated by reference. This enables clean high level multiplex PCR amplification in nested PCR formats. This can be implemented directly as described in the second-stage multiplex reaction in the second-stage reaction zone 680.

Example 4

Sequencing multiple regions nested within a first-stage PCR amplicon is now described. In some situations it will be advantageous to determine the sequence of many regions of the first-stage PCR amplicon, illustratively derived from different second-stage amplicons nested within the first-stage PCR target. For example, mutations in TEM beta lactamase that confer the ESBL phenotype can be spread across the gene. One can amplify a large portion of the gene in the first-stage amplification reaction, and then amplify various smaller regions in second-stage PCR.

Figure 7A:
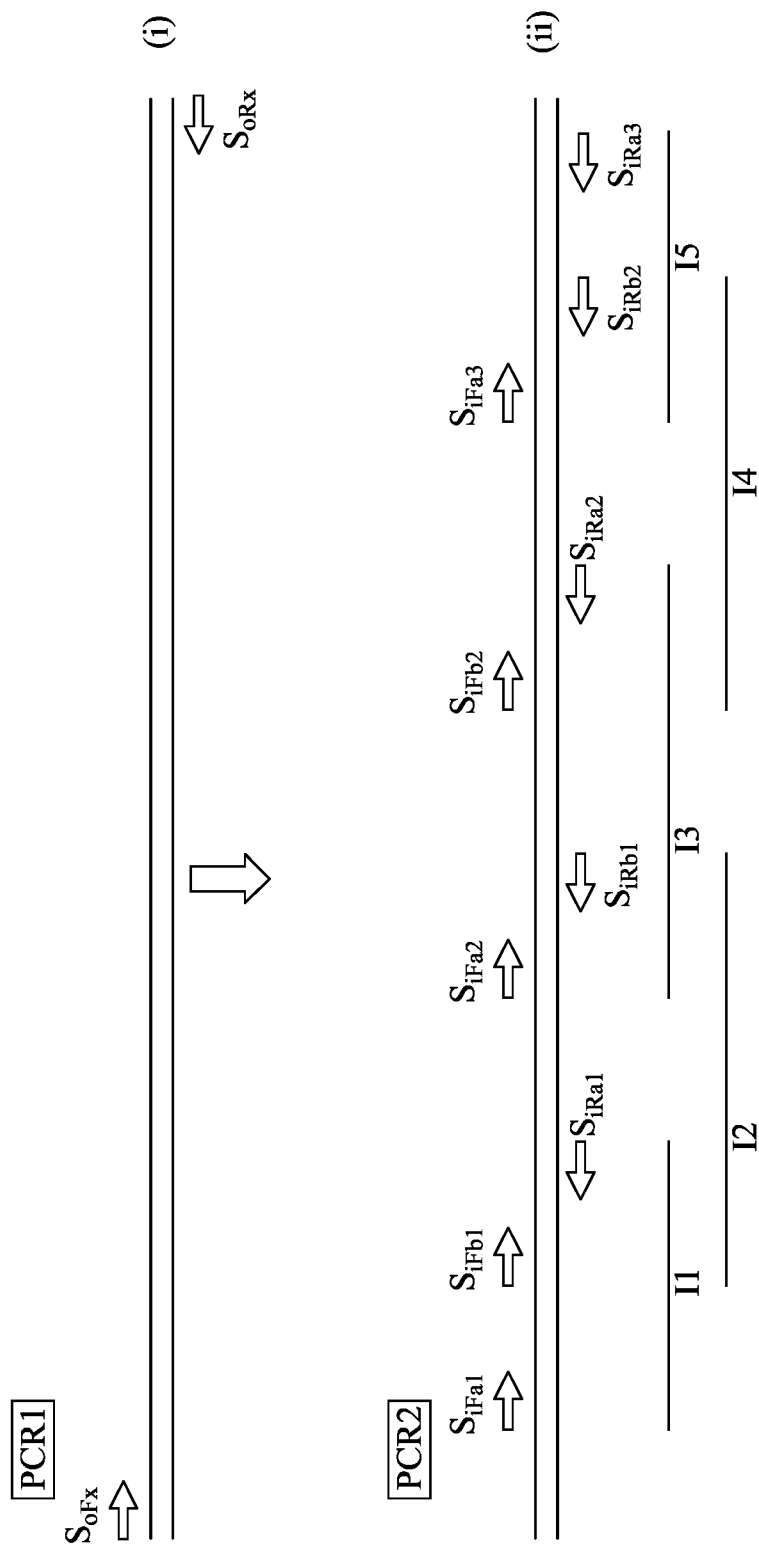
FIGS. 7A-C show an embodiment for sequencing multiple amplification products generated from a single first-stage amplicon.

In one illustrative example, overlapping amplicons are generated in second-stage PCR. When performed in discrete reactions, such as in wells 582 of the device of FIG. 1, these overlapping amplicons can be easily generated. In the array 681 of FIG. 4, the specificity of the amplification comes from the primers attached to the array spot 682. However, the primers in solution and the primers on the spots 682 may overlap (see FIG. 7A (i)-(ii)) in such a manner that instead of making a discrete set of overlapping second-stage amplicons (I1 to I5 in FIG. 7A(i)), even shorter amplicons may be generated (for example between $S_{iFb1}$ and $S_{iRa1}$, which would generate an amplicon that is only the portion of I1 and I2 that overlaps) that do not overlap and that do not completely cover the sequence.

Figure 7B:
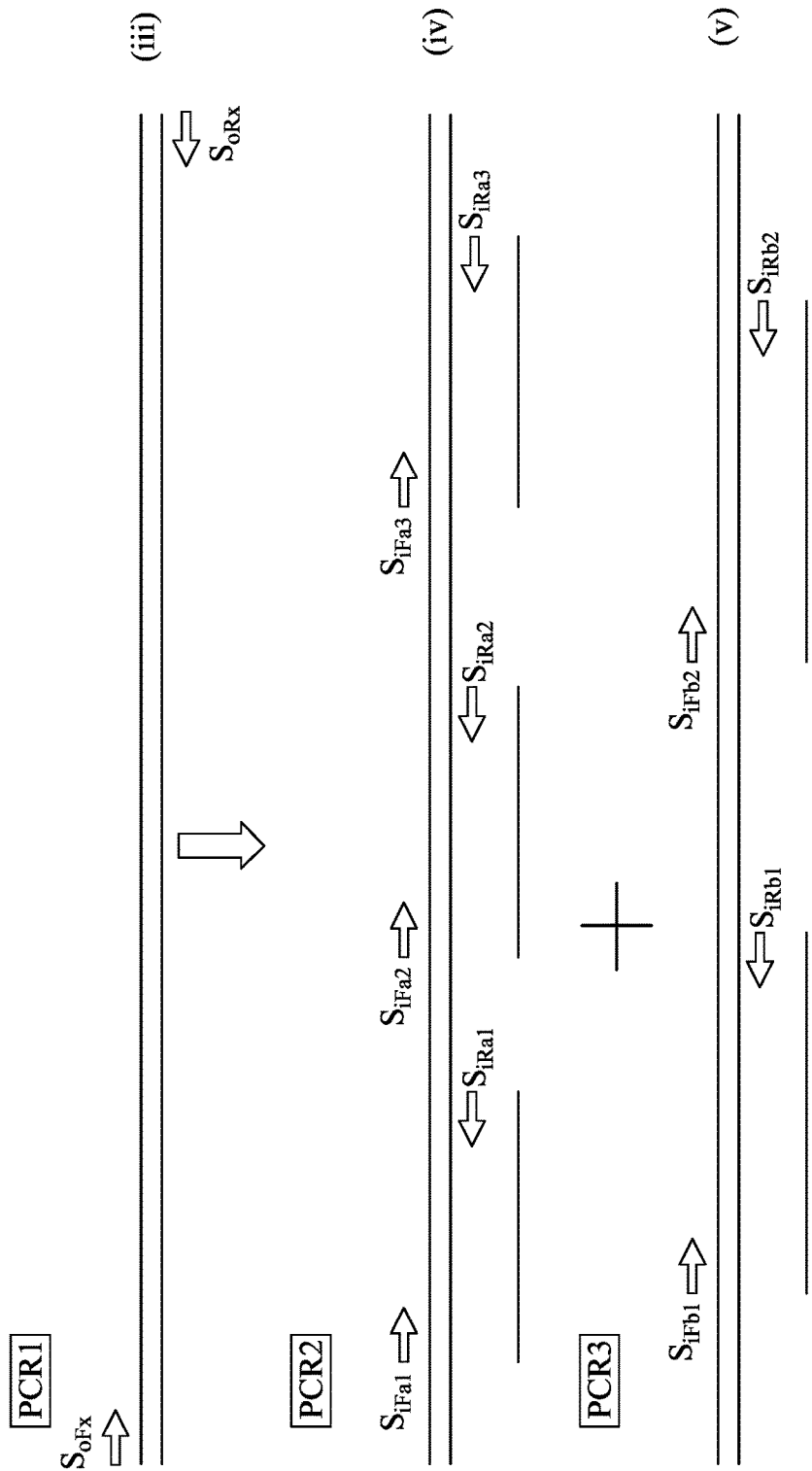
Figure 7C:
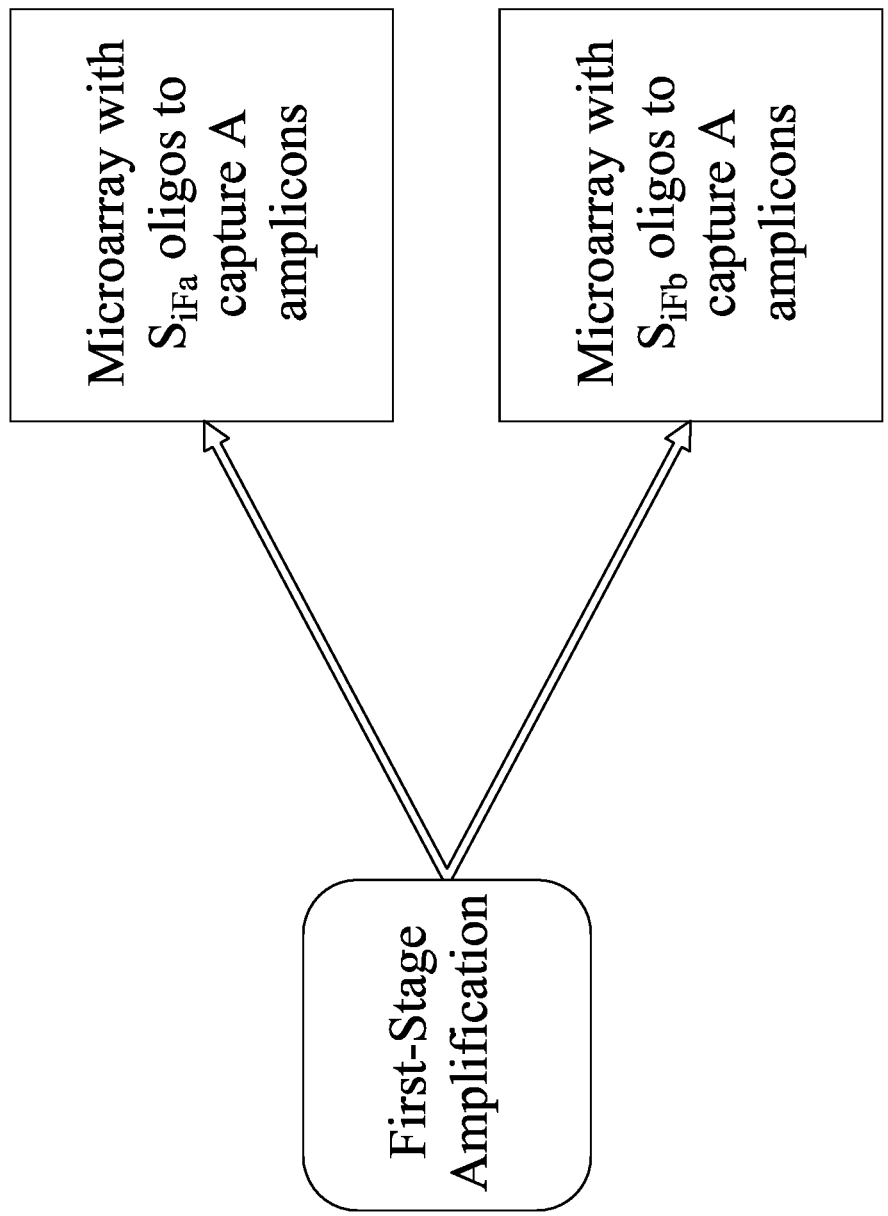

This problem may be avoided by splitting the second-stage PCR into two compartments, both similar to second-stage amplification zone 680, with two sets of reactions (FIGS. 7B and 7C). In this implementation the amplicons generated in second-stage A (FIG. 7B (iv)) are not overlapping so that undesired short amplicons are minimized or eliminated. The intervening amplicons are generated in second-stage B (FIG. 7B (v)), and they similarly are not overlapping, so that the undesired short amplicons are similarly minimized or eliminated.

Example 5

Figure 8A:
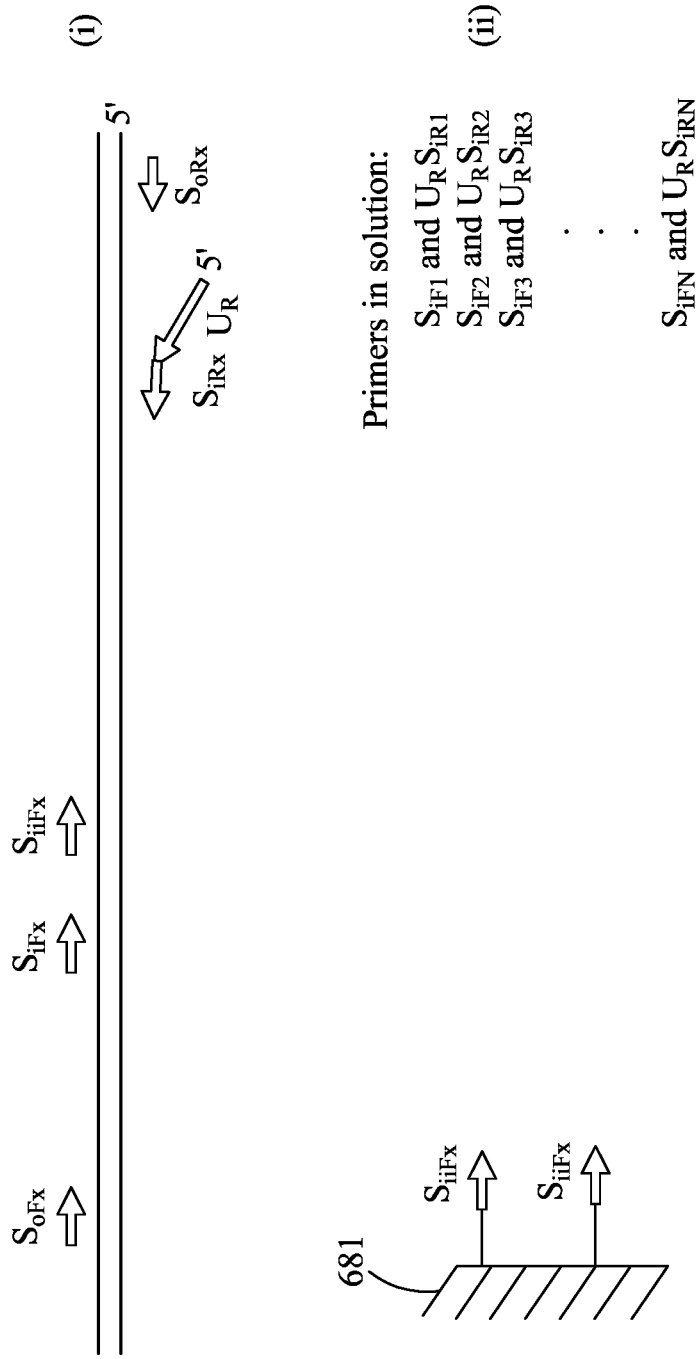
FIGS. 8A-8C are similar to FIGS. 5A-5C, except showing an alternative primer embodiment.
Figure 8B:
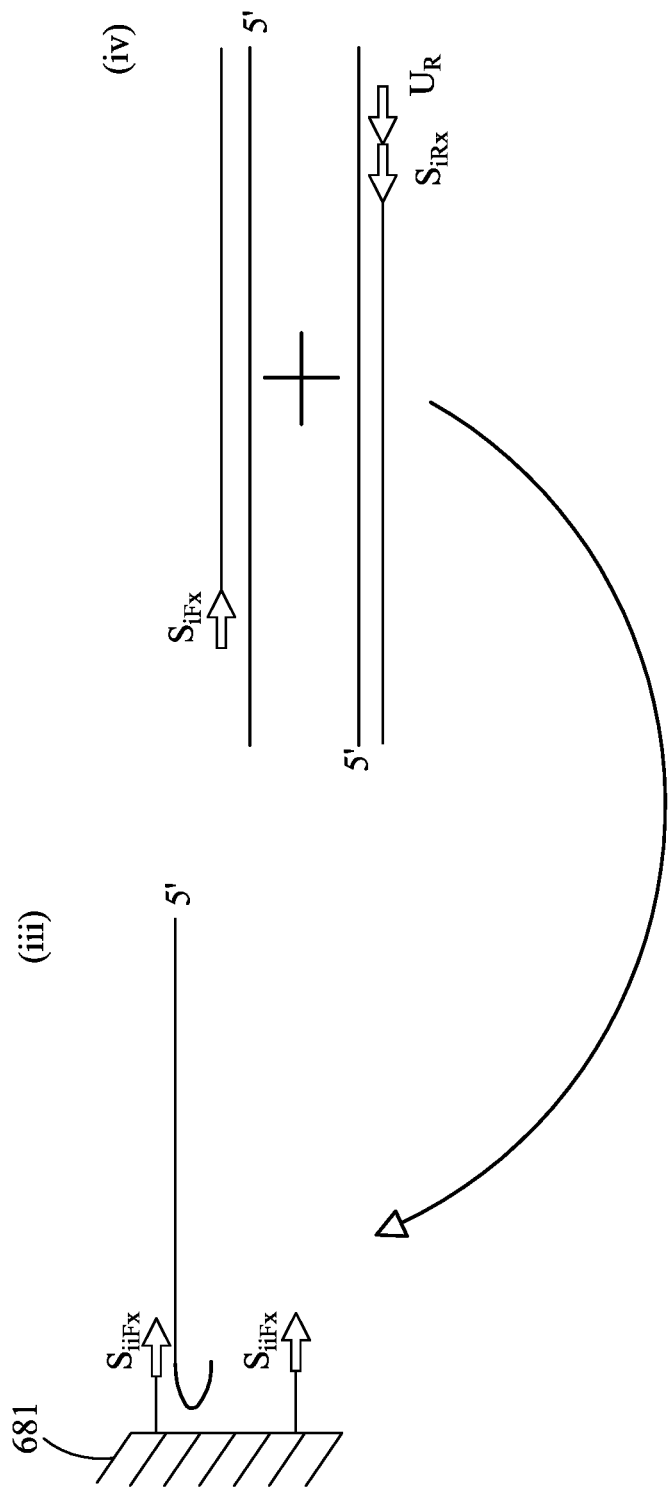
Figure 8C:
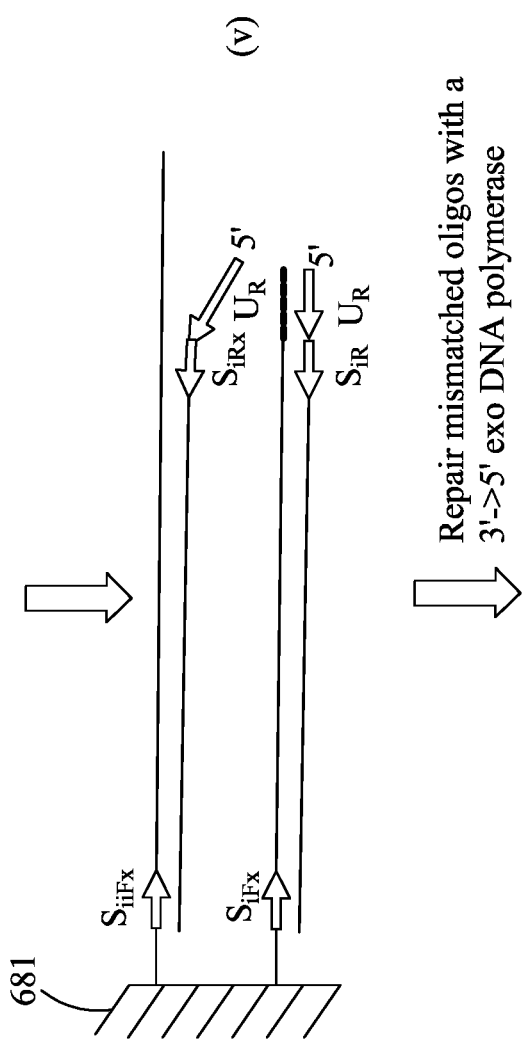

This implementation is similar to Example 3 above, except that all of the inner primers are present in the mixture (FIG. 8A). This has the advantage that amplification in solution together with amplification on the array is fast and efficient (FIG. 8B). To add an optional filter for specificity of the single molecular species that is synthesized on array 681, the capture primers may be "inner-inners". The inner-inners $S_{iiFx}$ hybridize to a sequence internal to the solution-based inner primers $S_{iFx}$, which is internal to the outer primers $S_{oFx}$ (see FIG. 8A (i)). The inner-inner primer $S_{oFx}$ can partially overlap with the inner primer $S_{iFx}$ in that direction as long as a few bases (illustratively at least 4 bases) are internal to (or 3' of) the $S_{iFx}$ sequence. Solution-based PCR takes place using the inner primers $S_{iFn}$ and $U_R S_{iRn}$, as shown in FIG. 8B (iv), and simultaneously on array 682, as shown in FIG. 8B (iii), resulting in a tethered amplicon having the appropriate universal primer, as shown in FIG. 8C (v). In this embodiment, because added specificity is provided using the two sets of nested primers $S_{iFx}$ and $S_{iiFx}$, it is understood that first-stage amplification with $S_{oFx}$ is optional, and that all amplification may take place in a single amplification chamber. Preparing array 681 for sequencing may be according to any of the methods discussed above.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and in the attached invention disclosure for purposes of illustrating the invention, it will be apparent to those skilled in the art that various changes in the methods and apparatus disclosed herein may be made without departing from the scope of the invention, which is defined in the appended claims. All changes which come within the meaning and range of equivalency of the claims are to be embraced within their scope.

The invention claimed is:

1. A method for two-step amplification and sequencing of a plurality of nucleic acids that may be in a sample, comprising:
    (a) amplifying the nucleic acids in a first mixture comprising a plurality of first-stage pairs of primers, each first-stage pair of primers configured for amplification of one of the plurality of nucleic acids to generate a first-stage amplicon for each of the nucleic acids that are present in the sample;
    (b) amplifying the first-stage amplicons using a plurality of second-stage pairs of primers, each second-stage pair of primers configured for amplification of one of the first-stage amplicons, wherein at least one of each pair of second-stage primers is nested within its corresponding first-stage pair of primers, to generate a single molecular species for each of the nucleic acids that are present in the sample; and
    (c) sequencing the single molecular species that are generated in step (b) without using a filter between steps (b) and (c).

2. The method of claim 1, wherein steps (b) and (c) are performed in a single reaction chamber.

3. The method of claim 1, wherein at least one of each pair of second-stage primers is tethered to a solid support.

4. The method of claim 1, wherein steps (b) and (c) are performed in different reaction vessels.

5. The method of claim 1, wherein steps (a) through (c) are performed in a single container, wherein step (a) is performed in a first-stage amplification chamber, and wherein steps (b) and (c) are performed in an array of second-stage amplification wells.

6. The method of claim 5, wherein steps (a) through (c) are performed in about 5 hours or less.

7. The method of claim 5, wherein all second-stage amplification wells are subjected to sequencing conditions.

8. The method of claim 5, further comprising the step of detecting whether the first-stage amplicon has been generated in each second-stage amplification well to generate a positive call for each second-stage amplification well where that amplicon has been generated.

9. The method of claim 8, wherein step (c) is performed only on those second-stage amplification wells where there is the positive call.

10. A method for two-step amplification and sequencing of a plurality of nucleic acids that may be in a sample, comprising:
    amplifying the nucleic acids in a first mixture comprising a plurality of first-stage pairs of primers, each first-stage pair of primers configured for amplification of one of the plurality of nucleic acids to generate a first-stage amplicon for each of the nucleic acids that are present in the sample;
    amplifying the first-stage amplicons using a plurality of second-stage pairs of primers, each second-stage pair of primers configured for amplification of one of the first-stage amplicons, wherein at least one of each pair of second-stage primers is nested within its corresponding first-stage pair of primers, to generate a single molecular species for each of the nucleic acids that are present in the sample; and
    sequencing the single molecular species generated in the second amplification without using a filter between the second amplification and the sequencing wherein no filter is used between the first amplification and the second amplification to identify a correct first-stage amplicon.

11. The method of claim 10, wherein the second amplification and the sequencing are performed in a single reaction chamber.

12. The method of claim 10, wherein at least one of each pair of second-stage primers is tethered to a solid support.

13. The method of claim 10, wherein the second amplification and the sequencing are performed in different reaction vessels.

14. The method of claim 10, wherein the method is performed in a single container, wherein the first amplification is performed in a first-stage amplification chamber, and the second amplification and the sequencing are performed in an array of second-stage amplification wells.

15. The method of claim 14, wherein the method is performed in about 5 hours or less.

16. The method of claim 14, wherein all second-stage amplification wells are subjected to sequencing conditions.

17. The method of claim 14, further comprising detecting whether the first-stage amplicon has been generated in each second-stage amplification well to generate a positive call for each second-stage amplification well where that amplicon has been generated.

18. The method of claim 17, wherein the second amplification is performed only on those second-stage amplification wells where there is the positive call.

\* \* \* \* \*

UNITED STATES PATENT AND TRADEMARK OFFICE
CERTIFICATE OF CORRECTION

PATENT NO. : 10,718,013 B2  
APPLICATION NO. : 15/574263  
DATED : July 21, 2020  
INVENTOR(S) : Mark Aaron Poritz et al.

Page 1 of 1

It is certified that error appears in the above-identified patent and that said Letters Patent is hereby corrected as shown below:

In the Claims

In Column 28, Line 58, please delete "without using a filter between the".
In Column 28, Line 59, please delete "second amplification and the sequencing".

Signed and Sealed this
Sixth Day of April, 2021

Drew Hirshfeld
*Performing the Functions and Duties of the*
*Under Secretary of Commerce for Intellectual Property and*
*Director of the United States Patent and Trademark Office*